(12) United States Patent
Perlin et al.

(10) Patent No.: US 8,255,061 B2
(45) Date of Patent: Aug. 28, 2012

(54) COMPACT MULTILEVEL ELECTRICAL INTEGRATION OF MICROSYSTEMS

(75) Inventors: Gayatri Eadara Perlin, Ann Arbor, MI (US); Brendan E. Casey, Ann Arbor, MI (US); Mayurachat Ning Gulari, Ann Arbor, MI (US); Kensall D. Wise, Ann Arbor, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 599 days.

(21) Appl. No.: 12/415,177

(22) Filed: Mar. 31, 2009

(65) Prior Publication Data

US 2010/0029148 A1 Feb. 4, 2010

Related U.S. Application Data

(60) Provisional application No. 61/084,344, filed on Jul. 29, 2008.

(51) Int. Cl.
*A61N 1/00* (2006.01)
*A61B 5/04* (2006.01)
(52) U.S. Cl. .................... 607/116; 600/377; 600/378
(58) Field of Classification Search .......... 600/372–373, 600/377–378, 383, 393–395, 544; 607/116
See application file for complete search history.

(56) References Cited

U.S. PATENT DOCUMENTS

| | | | | |
|---|---|---|---|---|
| 6,334,856 | B1 * | 1/2002 | Allen et al. | 604/191 |
| 2004/0006264 | A1 * | 1/2004 | Mojarradi et al. | 600/378 |
| 2007/0007240 | A1 * | 1/2007 | Wise et al. | 216/13 |

OTHER PUBLICATIONS

A. C. Hoogerwerf and K. D. Wise, "A three-dimensional microelectrode array for chronic neural recording," IEEE Transactions on Biomedical Engineering, vol. 41, No. 12, pp. 1136-1146, Dec. 1994.
A. M. Sodagar, G. E. Perlin, Y. Yao, K. D. Wise, and K. Najafi, "An implantable microsystem for wireless multi-channel cortical recording," in Proc. of the Solid State Sensors, Actuators, and Microsystems Conference (Transducers), 2007, pp. 69-72.
B. Humphrey, "Using parylene for medical substrate coating," Medical plastics and Biomaterials, p. 28, Jan. 1996.
C. Kim and K. D. Wise, "A 64-site multishank CMOS low-profile neural stimulating probe," IEEE Journal of Solid-States Circuits, vol. 31, No. 9, pp. 1230-1238, Sep. 1996.

(Continued)

*Primary Examiner* — Linda Dvorak
*Assistant Examiner* — Brian M Antiskay
(74) *Attorney, Agent, or Firm* — Harness, Dickey & Pierce, P.L.C.

(57) ABSTRACT

A microsystem comprising a substrate having an aperture formed therethrough. The aperture includes a first cross-section and a second cross-section—the first cross-section being smaller than the second cross-section to define a ledge therebetween. A probe member is disposed within the aperture of the substrate, such that a backend of the probe member defines a cross-section that is greater than the first cross-section of the aperture and smaller than the second cross-section such that the probe member engages the ledge. A plurality of probe shanks extend from the probe member. Each of the probe shanks includes a plurality of leads disposed there along. Each of the leads extending from the probe shanks to an opposing side of the probe member.

15 Claims, 23 Drawing Sheets

OTHER PUBLICATIONS

D. F. Lemmerhirt and K. D. Wise, "Air-isolated through-wafer interconnects for microsystem applications," Proceedings of the Solid-State Sensors, Actuators, and Microsystems (Transducers), 2003, pp. 1067-1070.

E. M. Schmidt, J. S. Mcintosh and M. J. Bak, "Long-term implants of parylene-C coated microelectrodes," Med. Biol. Eng. Comp., vol. 26, 1988, pp. 96-101.

G. E. Loeb, M. J. Bak, M. Salcman and E. M. Schmidt, "Parylene as a chronically stable, reproducible microelectrode insulator," IEEE Trans. Biomed. Eng., vol. 24, 1977, pp. 121-128.

G. Phipps, "Wire bond vs. flip chip packaging: a technical trade-off analysis," Advanced Packaging, vol. 14, No. 7, Jul. 2005.

Gaiser Tool Company, Publications: Single Point T.A.B., pp. 133-145.

I. W. Qin, "Wire bonding tutorial: advances in bonding technology," Advanced Packaging, vol. 14, No. 7, Jul. 2005.

J.-M. Hsu, S. Kammer, E. Jung, L. Rieth, R. A. Normann, and F. Solzbacher, "Characterization of Parylene-C film as an encapsulation material for neural interface devices," Proc. of the Conference on Multi-Material Micro Manufacture, Oct. 2007, pp. 16-23.

K. Najafi, "Solid state microsensors for cortical nerve recordings," IEEE Engineering in Medicine & Biology, pp. 375-387, Jun./Jul. 1994.

K. Najafi, J. Ji, and K. D. Wise, "Scaling limitations of silicon multichannel recording probes," IEEE Transactions on Biomedical Engineering, vol. 37, No. 1, pp. 1-11, Jan. 1990.

L. Wolgemuth, "Assessing the performance and suitability of parylene coating," Medical Device and Diagnostic Industry, vol. 22, 2000, p. 42-49.

M. Topper et al., "Biocompatible hybrid flip chip microsystem—integration for next generation wireless neural interfaces," In Proc. of the Electronic Components and Technology Conference (ECTC), 2006, pp. 705-708.

P. Rousche, D. S. Pellinen, D. P. Pivin, J. C. Williams, R. J. Vetter, and D. R. Kipke, "Flexible polyimide-based intracortical electrode arrays with bioactive capability," IEEE Transactions on Biomedical Engineering, vol. 48, No. 3, pp. 361-370, Mar. 2001.

P. T. Bhatti and K. D. Wise, "A 32-site 4-channel high density electrode array for a cochlear prosthesis," IEEE Journal of Solid-State Circuits, vol. 41, No. 12, pp. 2965-2973, Dec. 2006.

P.K. Campbell, K. E. Jones, R. J. Huber, K. W. Horch, and R.A. Normann, "A silicon-based, three-dimensional neural interface: manufacturing processes for an intracortical electrode array," IEEE Transactions on Biomedical Engineering, vol. 38, No. 8, pp. 758-766, Aug. 1991.

Q. Bai, K. D. Wise, J. F. Hetke, and D. J. Anderson, "A microassembly structure for intracortical three-dimensional electrode arrays," in Proceedings of the 18th Annual International Conference of the IEEE Engineering in Medicine and Biology Society (EMBC), 1996, pp. 264-265.

S. Kim, M. Wilke, M. Klein, M. Topper, and F. Solzbacher, "Electromagnetic compatibility of two novel packaging concepts of an inductively powered neural interface," in Proc. of the IEEE/EMBS Conference on Neural Engineering, 2007, pp. 434-437.

S. Takeuchi, T. Suzuki, K. Mabuchi, and H. Fujita, "3D flexible multichannel neural probe array," Journal of Micromechanical Microengineering, vol. 14, pp. 104-107, 2004.

Y. Yao, M. N. Gulari, J. F. Hetke, and K. D. Wise, "A low-profile three-dimensional neural stimulating array with on-chip current generation," in Proceedings of the 26th Annual International Conference of the IEEE Engineering in Medicine and Biology Society (EMBC), 2004, pp. 1994-1997.

\* cited by examiner

102

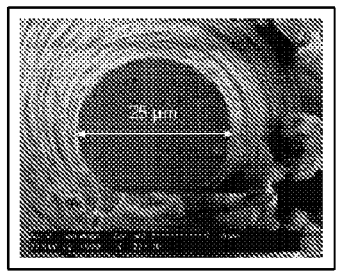 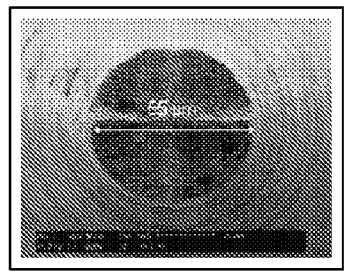 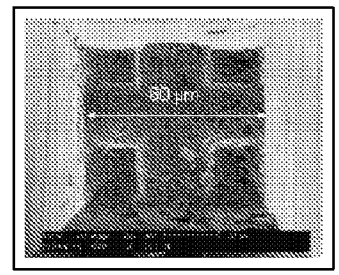
Fig-14A   Fig-14B   Fig-14C
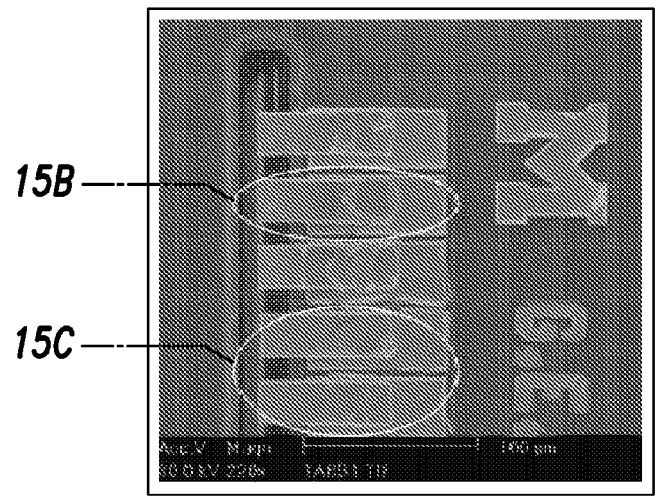
Fig-15A
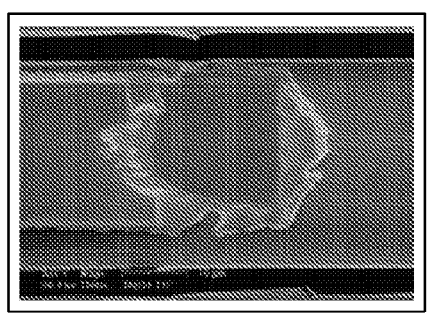 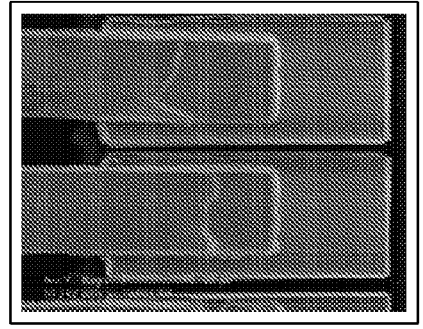
Fig-15B   Fig-15C

COMPACT MULTILEVEL ELECTRICAL INTEGRATION OF MICROSYSTEMS

CROSS-REFERENCE TO RELATED APPLICATIONS

This application claims the benefit of U.S. Provisional Patent Application No. 61/084,344, filed Jul. 29, 2008. The entire disclosure of the above application is incorporated herein by reference.

GOVERNMENT INTEREST

This invention was made with government support under Grant No. EEC9986866 awarded by the National Science Foundation. The government has certain rights in the invention

FIELD

The present disclosure relates to microsystems and, more particularly, relates to methods for compact multilevel electrical integration of microsystems.

BACKGROUND

The statements in this section merely provide background information related to the present disclosure and may not constitute prior art.

Many applications in neuroscience and neural prosthetics would benefit from having three-dimensional arrays of electrodes to allow the simultaneous monitoring of interactions among networks of neurons spanning multiple layers of brain. However, creating practical three-dimensional arrays has remained a challenge. Typically, neural probes are batch fabricated using planar processing techniques, resulting in two-dimensional electrode configurations which have to be micro-assembled to form 3-D arrays. The existing assembly approaches are tedious and result in fragile and oversized devices. The present teachings present a novel approach to 3-D microelectrode array formation and wire overlay that enables easy high-yield assembly and pushes the limits of miniaturization.

Several approaches exist for electrically interfacing with neurons in a volume of tissue. The earliest, cheapest and most widely available method involves microwire arrays which are typically bundled together with tips staggered at different heights. A silicon-based alternative to the microwire solution was developed at the University of Utah. Although the physical structure of these arrays appears three-dimensional, neither can be considered true 3-D electrical interfaces because they lack multiple channels that simultaneously span the longitudinal, transverse and vertical dimensions. Two-dimensional arrays fabricated back-to-back that fold into 3-D arrays have also been demonstrated, but these are inherently limited to only two parallel sets of shanks.

True 3-D interfaces formed by assembling 2-D arrays in parallel have been demonstrated in the past. However, the assembly methods developed thus far are tedious, preventing the 3-D arrays from being supplied in quantity. The past approaches to assembling two-dimensional probes (passive or active) involve inserting the individual shanks 102 on each probe into corresponding holes formed in a thin silicon platform 104 and securing the multiple probes in parallel with orthogonally-fitted comb-like structures, called spacers, as shown in FIGS. 1(a)-(c) and 2(a)-(b). In this assembly process, the first step is to orthogonally bend the gold tabs on each probe wing such that they are parallel to the platform surface. In this state, the probe back end is held by a vacuum pick that is connected to a 3-way micromanipulator. Then the shanks are orthogonally aligned to the holes in the platform and dropped into the platform. This process is repeated for each probe making up the 3-D array. Next, the silicon spacer 106 is fitted and used to stabilize all probes, which otherwise would wobble due to the weight of the protruding back end 108. Finally with the probes in place and stabilized on the platform, the gold tabs on each probe wing 110 are ultrasonically bonded to the platform. A picture of an assembled 3-D array using four parallel active probes orthogonally assembled on a silicon platform and stabilized by silicon spacers 106 is shown in FIGS. 2(a)-(c).

This approach has a number of disadvantages. The 2-D arrays used for 3-D assembly are specifically designed with lateral wings that take significant space, not only from the device point of view but also on the mask. The thin silicon platform (~15 μm), defined by a boron etch-stop process, must carry the assembled probes and perhaps other integrated circuit components, and while it is supported on a solid metal block during assembly, it is fragile and difficult to use for multiple implants. The idea of individual holes in the platform for each shank has merit for encapsulation around each shank as was demonstrated with a glass frit reflow process, but results in a tedious assembly procedure since each shank must be precisely aligned before the entire probe can be inserted. Once all probes are inserted into the platform, they must be manually held in parallel relation while the spacer is being aligned and fitted. This is yet another tedious and time consuming step. In bonding the lead tabs, the bond wedge (typically 100 μm at the tip, tapering at 15°) must be able to access tabs in between the wings, limiting the array spacing. The bond wedge must also access the inner-most tab on each wing without interfering with the back end, which results in "dead" space on the wing that places the inner-most tab a minimum distance away from the back end of the probe. A substantial vertical rise of the array above the platform cannot be avoided even with passive probes since vertical spacers are used for stabilization. This is a major limitation, especially with active probes, that complicates or even prohibits the post-implant procedure of replacing the dura over the device. Although a folding back end technology was developed, the vertical rise is still of concern since multiple back ends are stacked on top of each other. Furthermore, the folding technique is not effortless. The successful assembly of just one 3-D array using the described approach can take an hour or more. Even then, these structures remain relatively large and fragile for fully implantable applications.

SUMMARY

According to the principles of the present disclosure, a microsystem is provided comprising a substrate having an aperture formed therethrough. The aperture includes a first cross-section and a second cross-section—the first cross-section being smaller than the second cross-section to define a ledge therebetween. A probe member is disposed within the aperture of the substrate, such that a back end of the probe member defines a cross-section that is greater than the first cross-section of the aperture and smaller than the second cross-section such that the probe member engages the ledge. A plurality of probe shanks extend from the probe member. Each of the probe shanks includes a plurality of leads disposed therealong, each of the leads extending from the probe shanks to an opposing side of the probe member.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

Figure 8A:
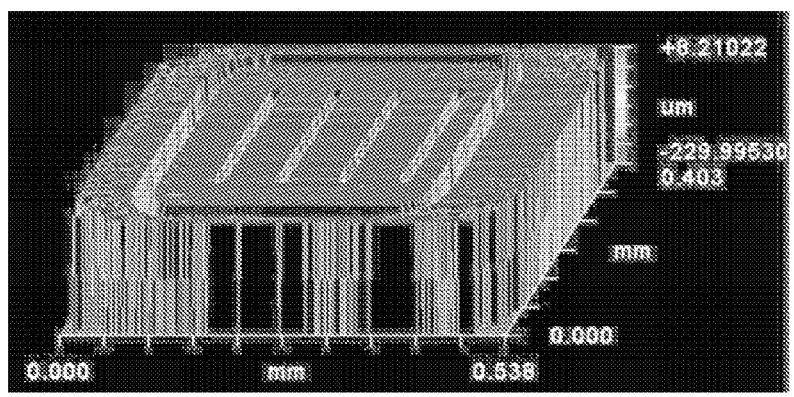
Figure 8B:
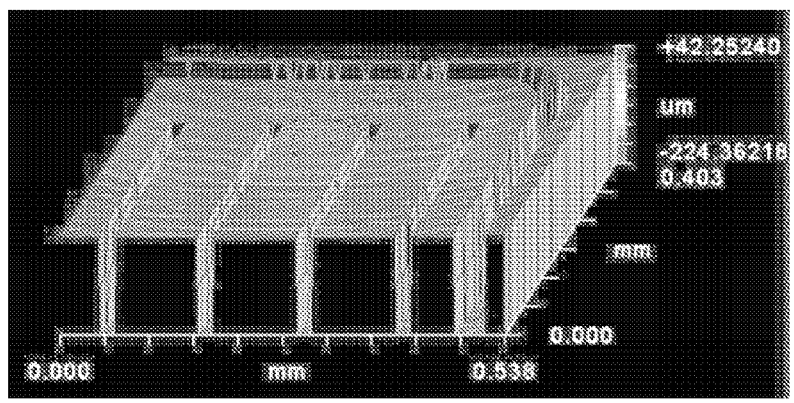
Figure 9:
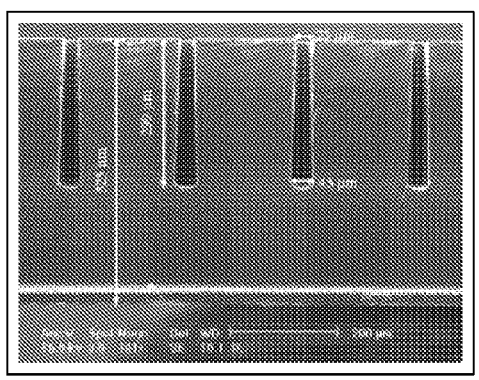
Figure 10:
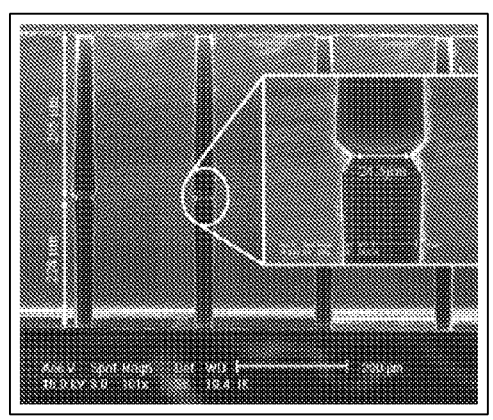
Figure 11A:
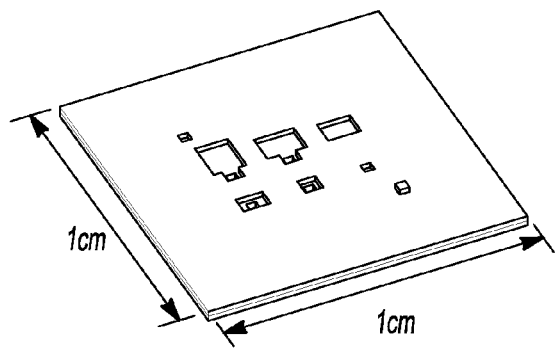
Figure 11B:
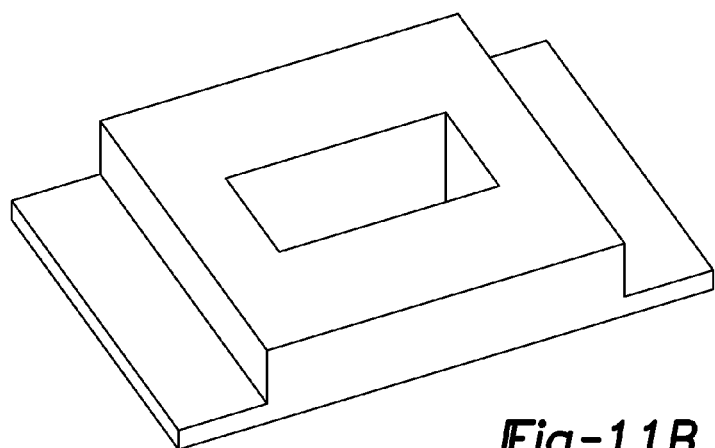
Figure 11C:
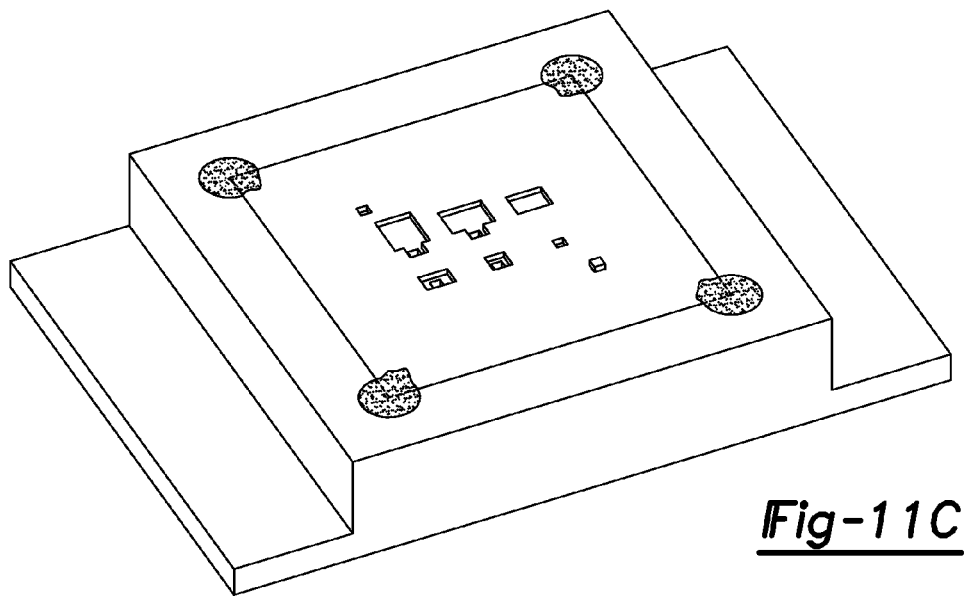
Figure 12A:
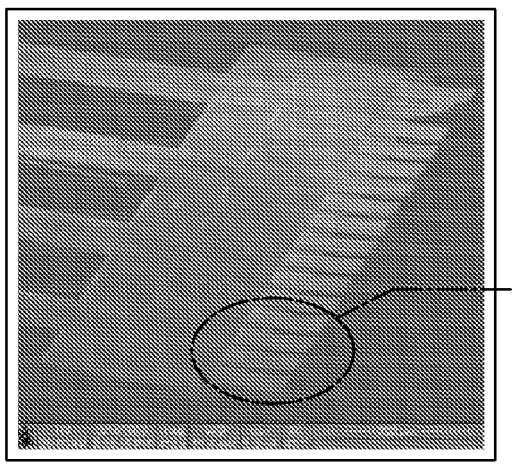
Figure 12B:
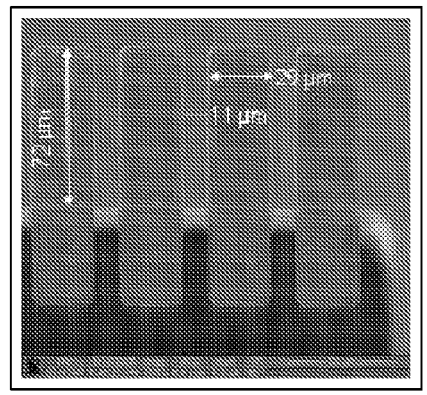
Figure 13A:
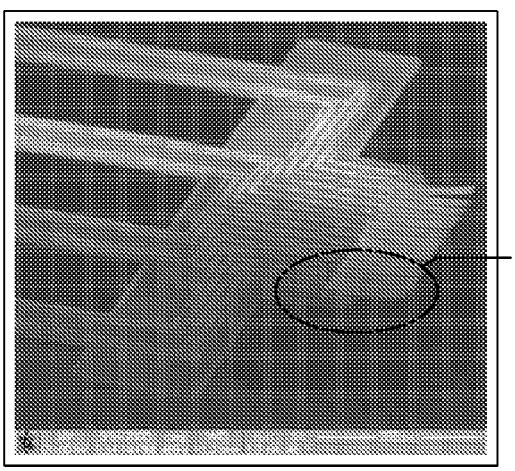
Figure 13B:
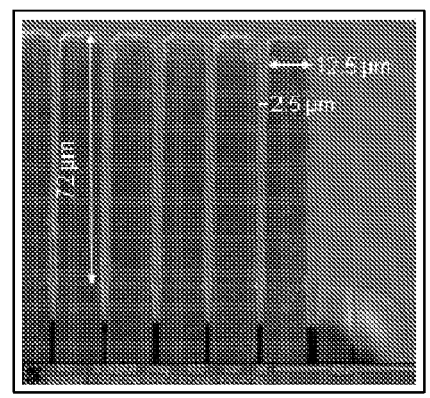
Figure 16A:
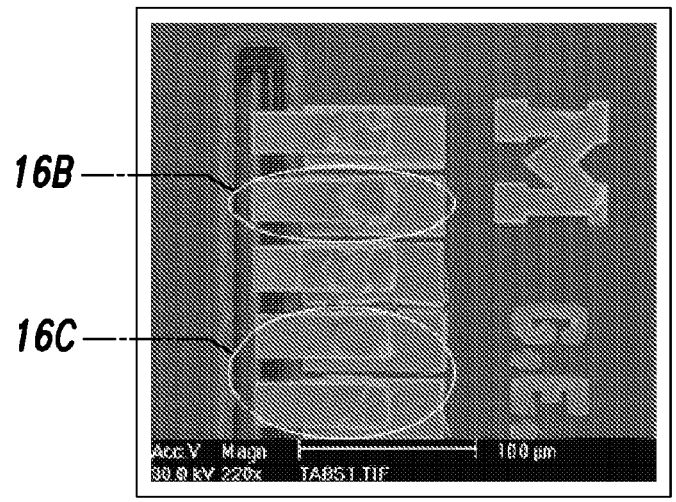
Figure 16B:
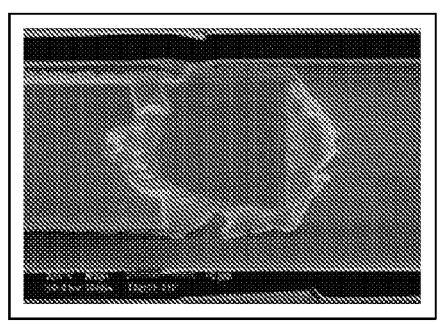
Figure 16C:
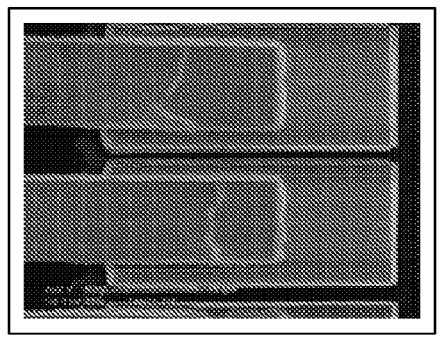
Figure 17:
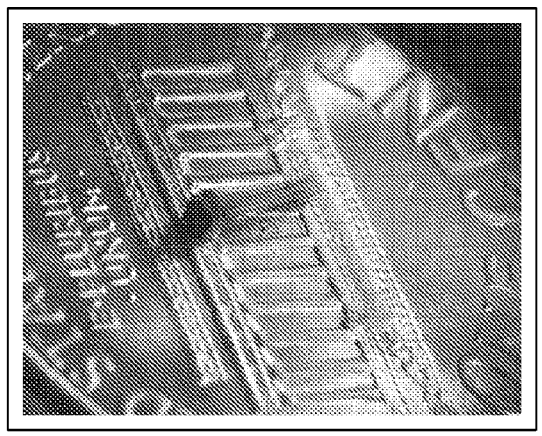
Figure 18A:
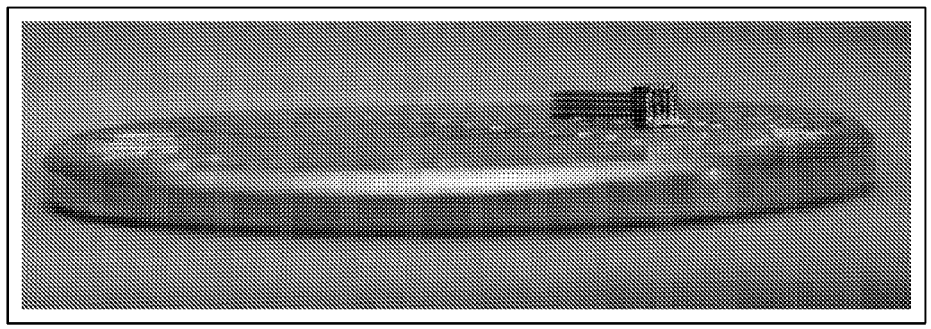
Figure 18B:
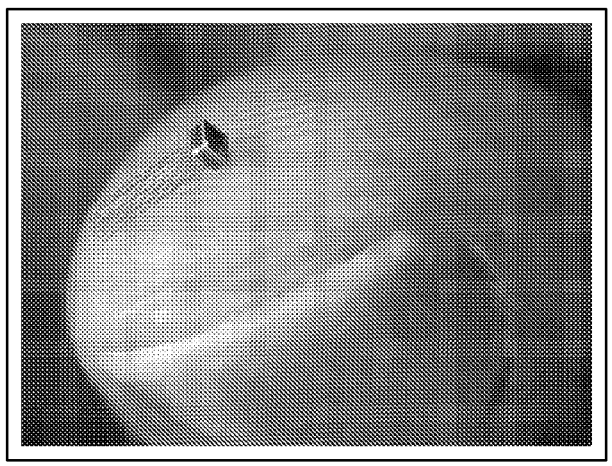
Figure 18C:
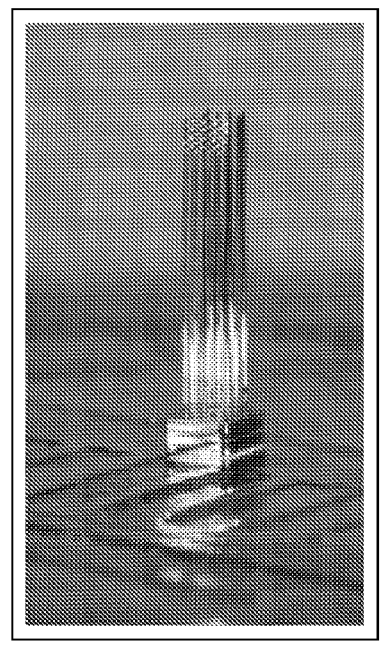
Figure 19A:
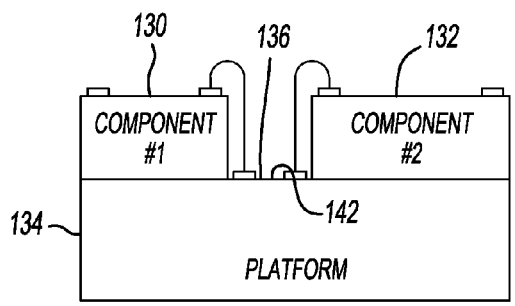
Figure 19B:
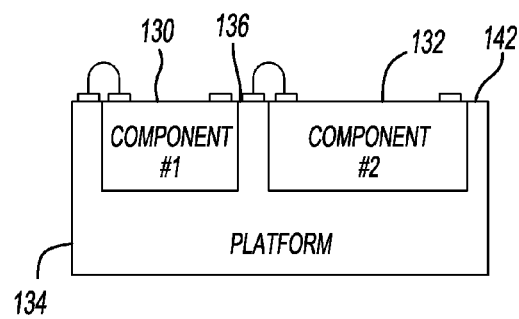
Figure 19C:
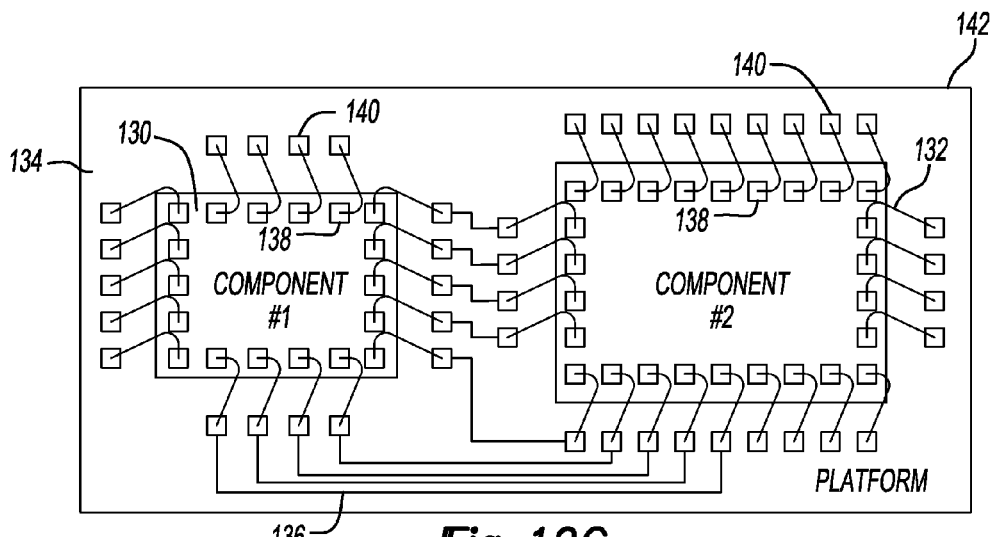
Figure 20A:
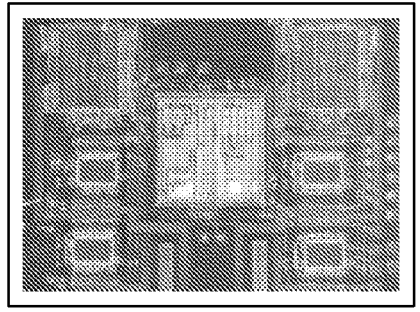
Figure 20C:
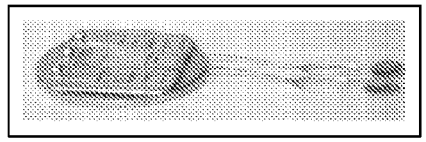
Figure 20B:
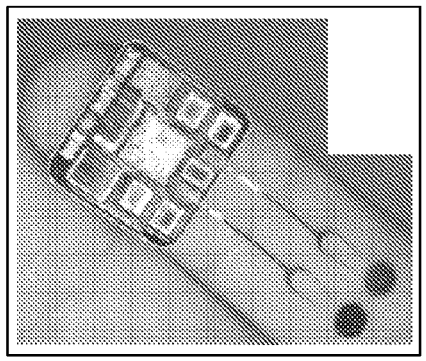
Figure 21:
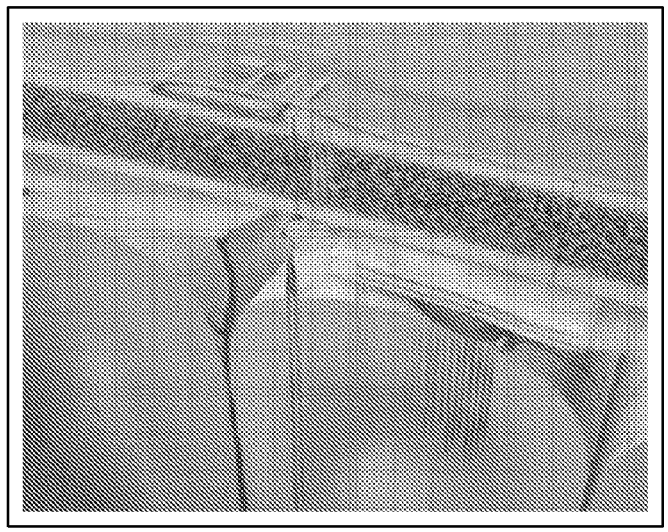
Figure 22A:
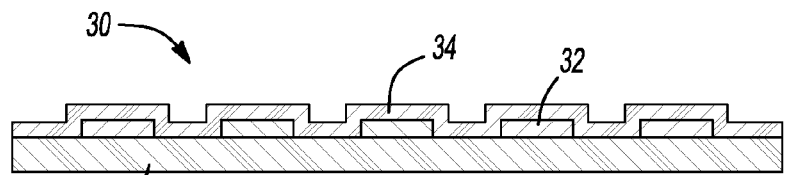
Figure 22B:
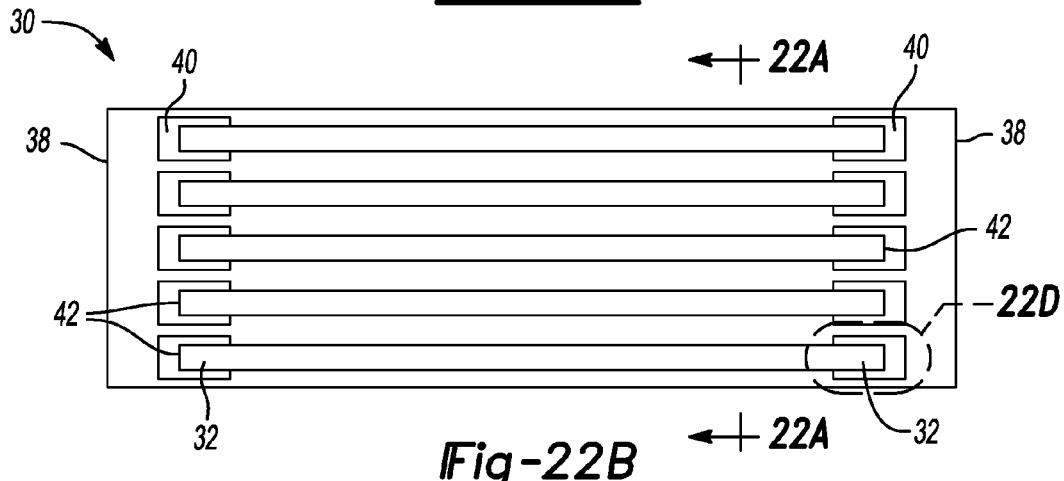
Figure 22C:
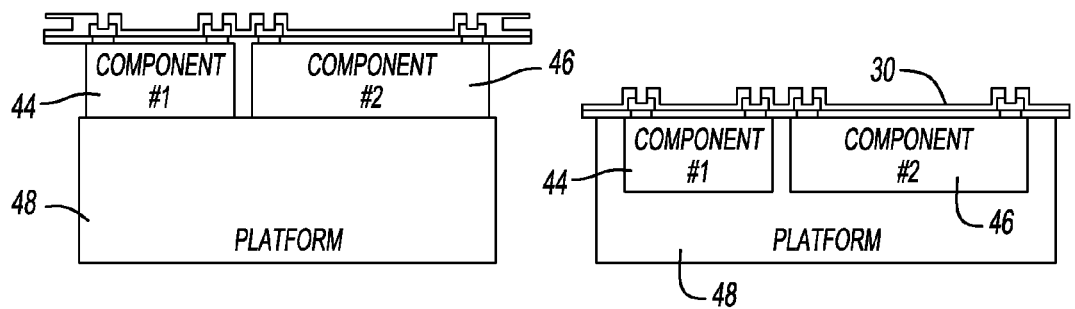
Figure 22D:
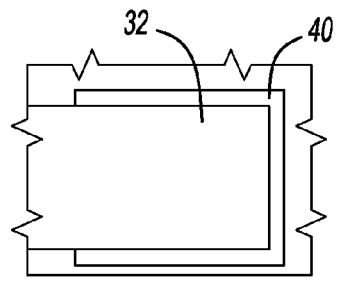
Figure 23A:
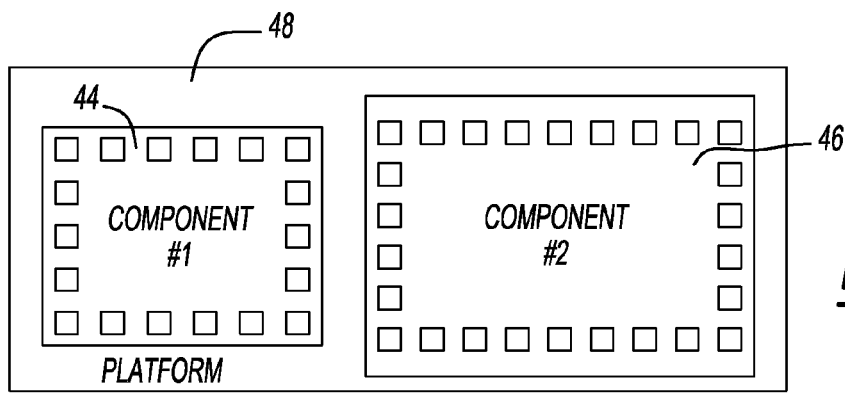
Figure 23B:
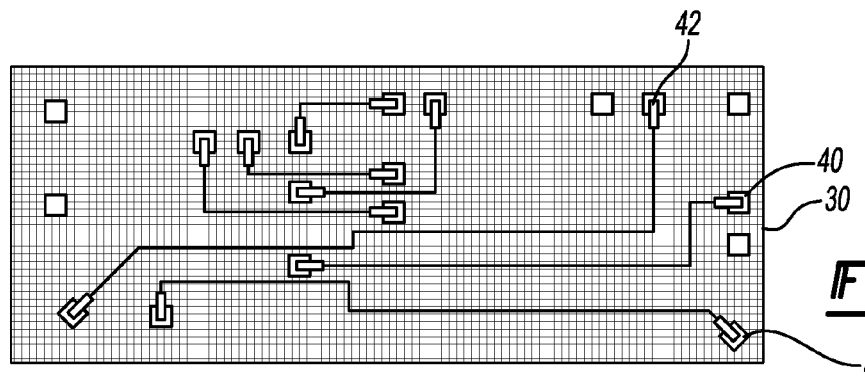
Figure 23C:
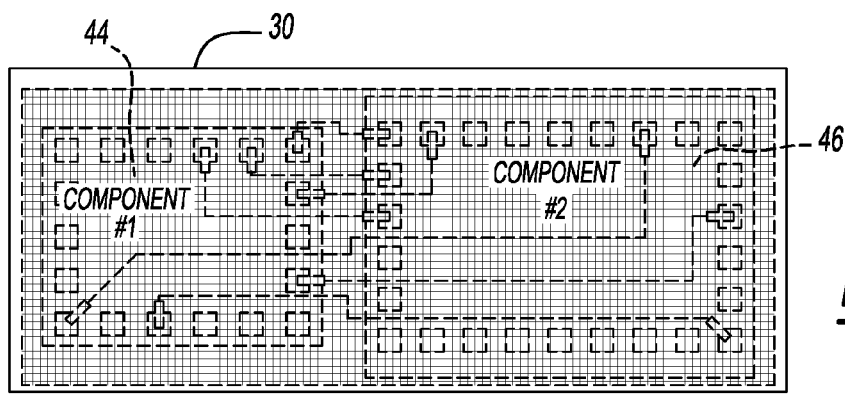
Figure 23D:
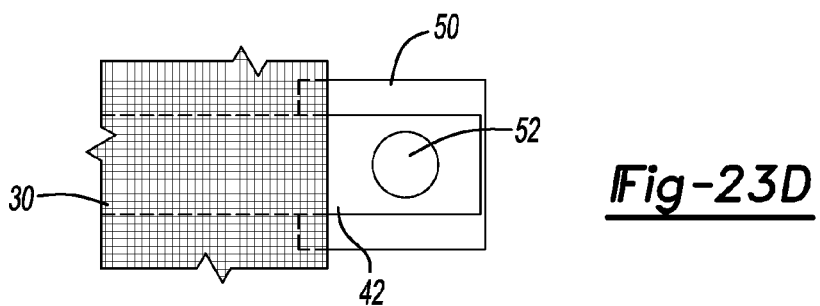
Figure 24:
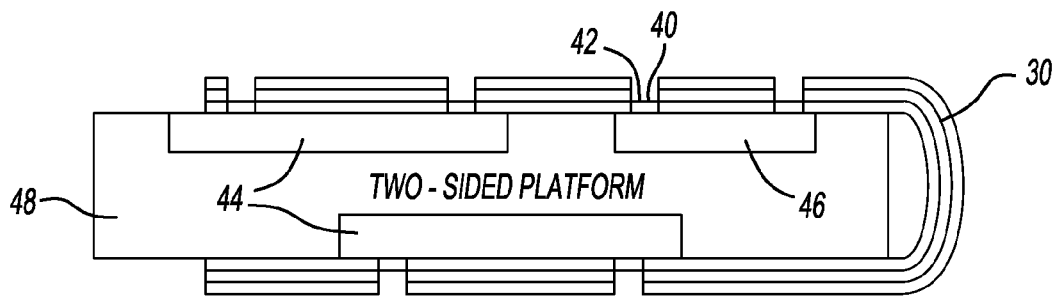
Figure 25A:
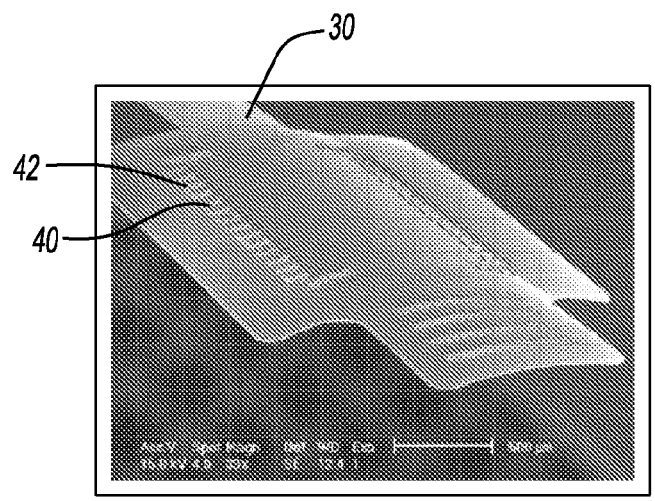
Figure 25B:
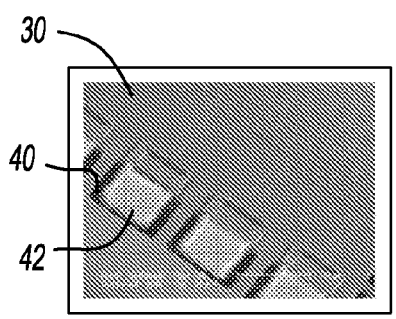
Figure 25C:
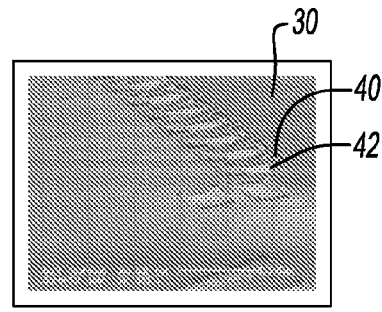
Figure 26A:
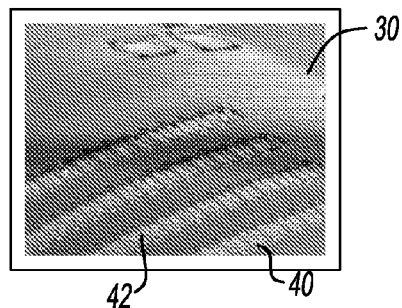
Figure 26B:
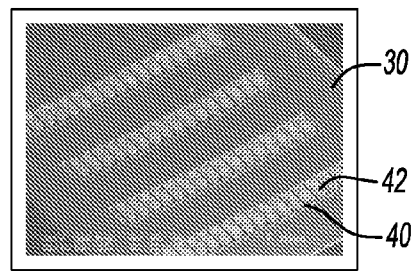
Figure 26C:
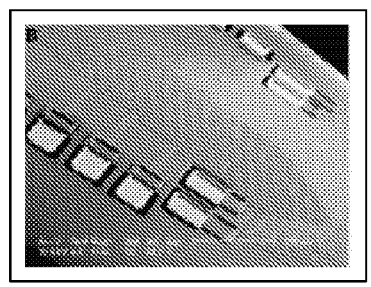
Figure 26D:
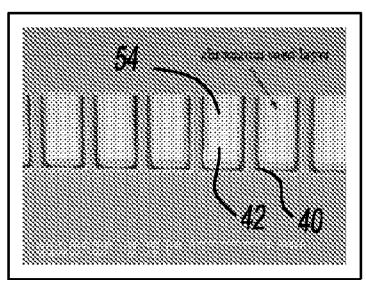
Figure 27A:
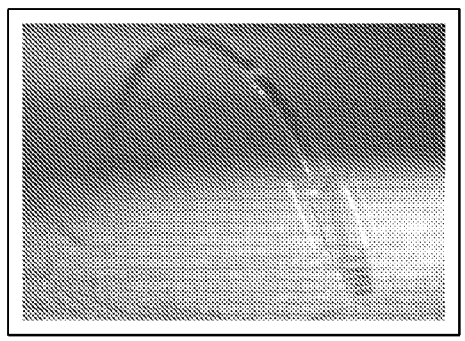
Figure 27B:
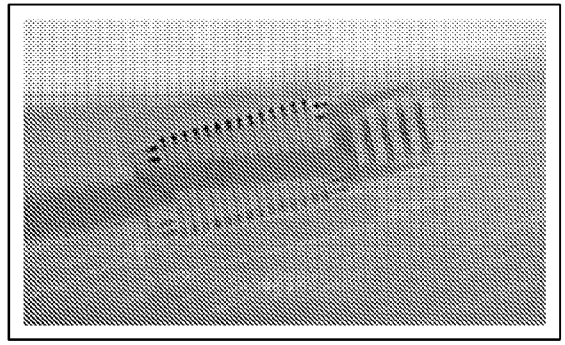
Figure 28A:
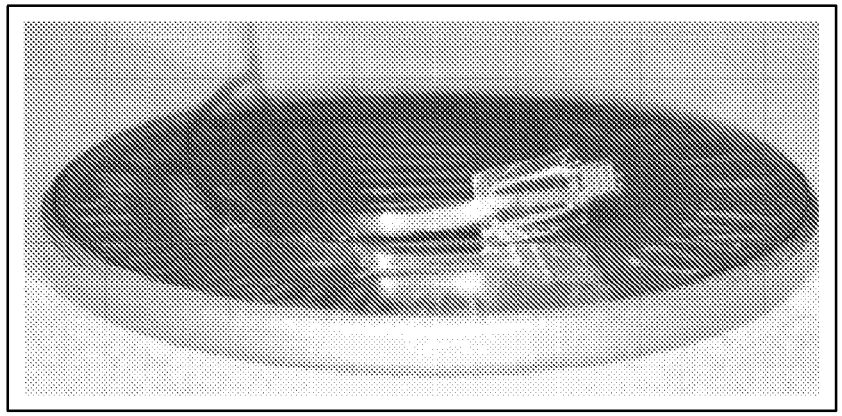
Figure 28B:
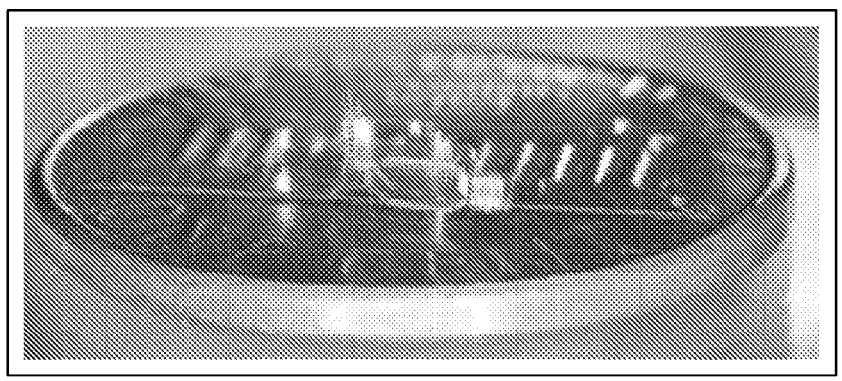
Figure 29:
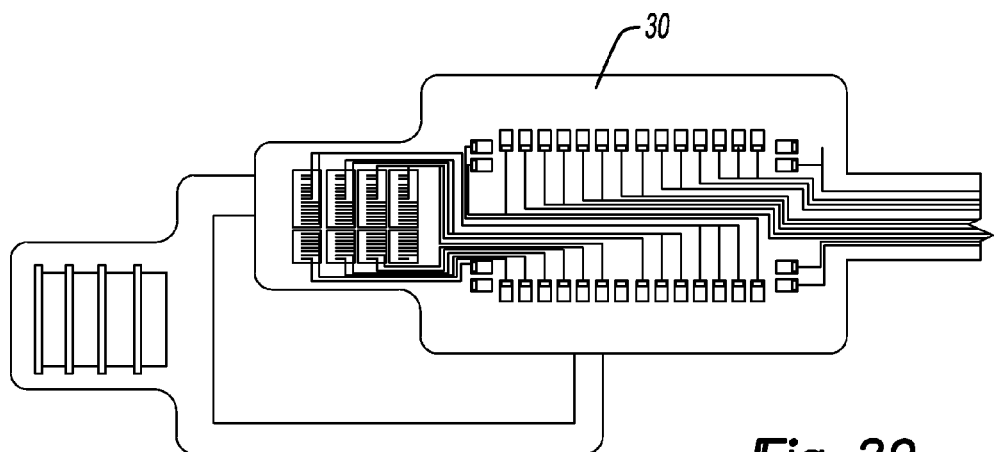
Figure 30A:
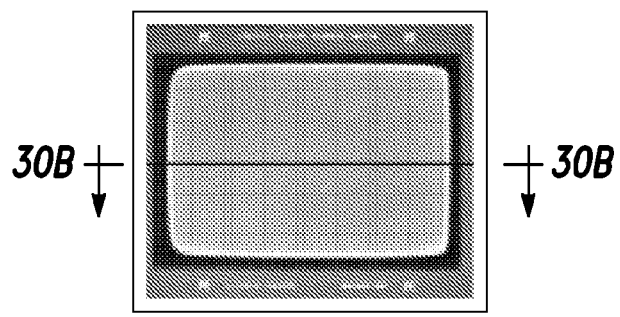
Figure 30C:
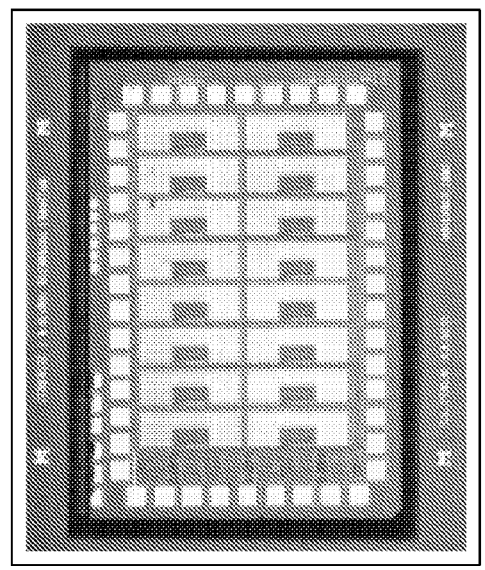
Figure 30B:
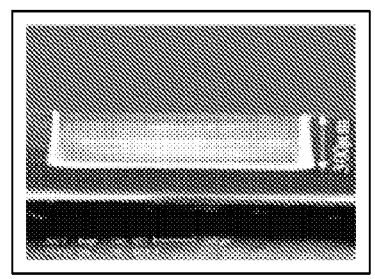
Figure 31A:
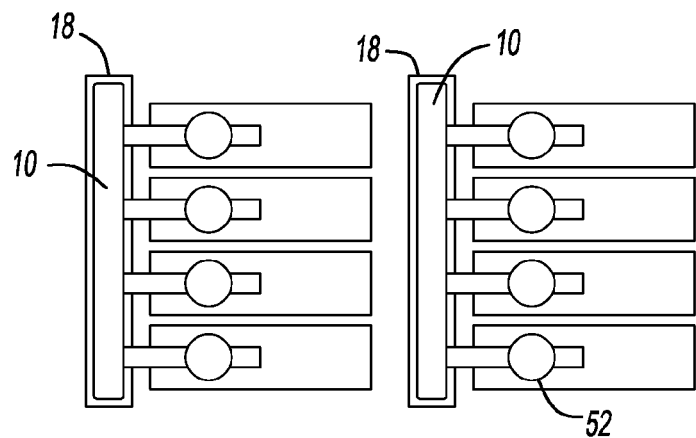
Figure 31B:
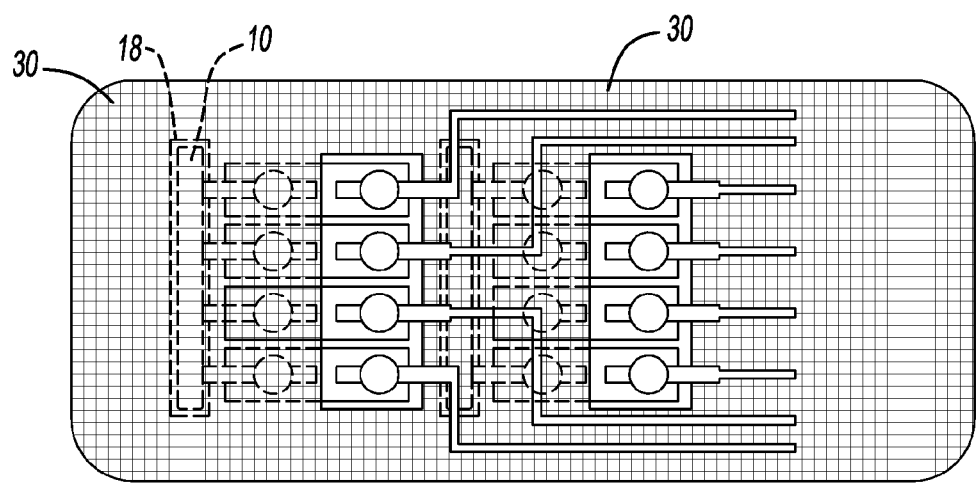
Figure 32A:
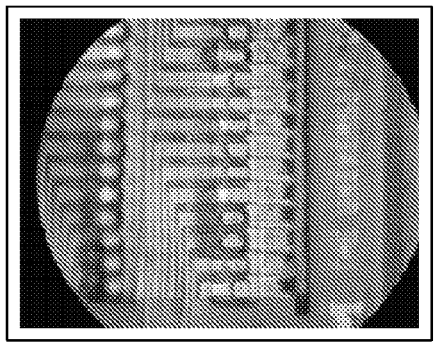
Figure 32E:
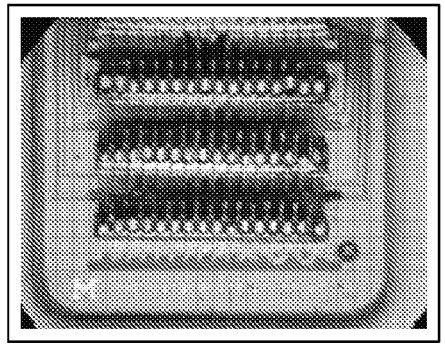
Figure 32B:
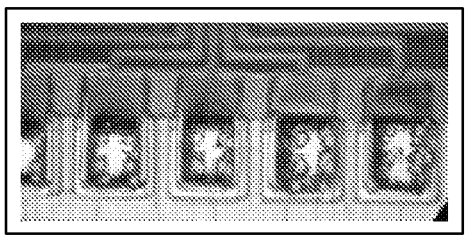
Figure 32F:
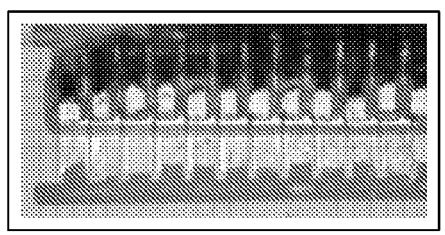
Figure 32C:
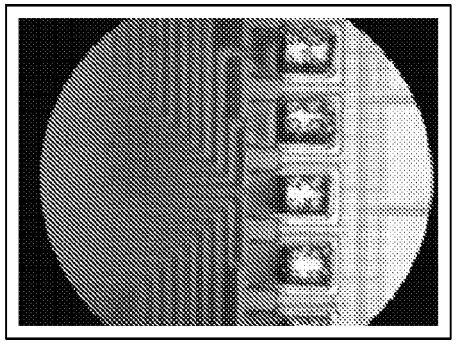
Figure 32G:
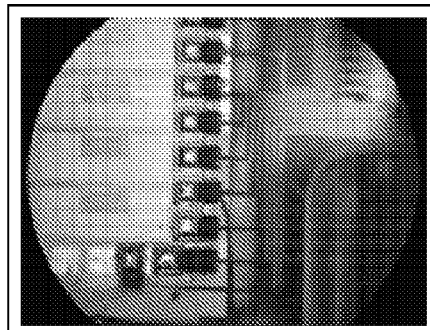
Figure 32D:
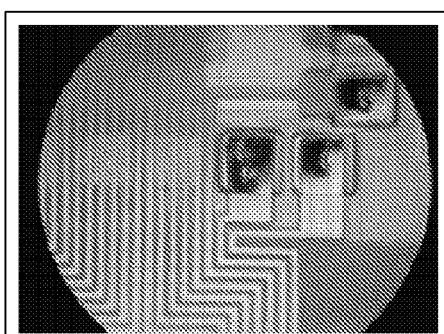
Figure 32H:
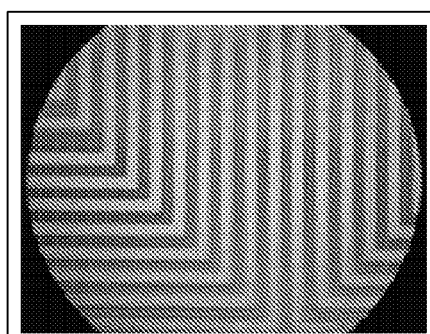
Figure 33:
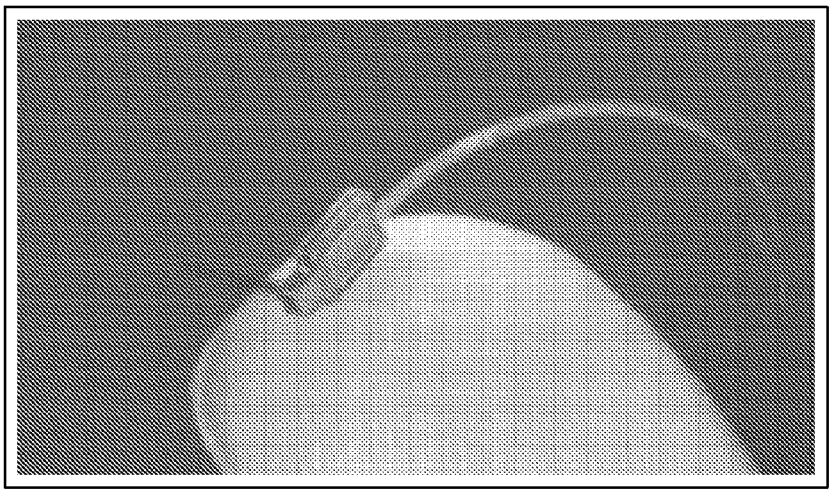

FIGS. 8(a) and 8(b) illustrate optical profilometer graphs showing the simultaneous etching of the slots and perimeter in the fabrication of the compact 3D array platform;

FIG. 9 illustrates an SEM picture showing the cross-sectional profile of slots etched 300 μm deep;

FIG. 10 illustrates an SEM picture showing the cross-section of DRIE etched slots in the case where the slot and perimeter openings are equal;

FIG. 11(a) illustrates a silicon assembly carrier;

FIG. 11(b) illustrates a metal support block for use with the silicon assembly carrier;

FIG. 11(c) illustrates the assembly jig employing the silicon assembly carrier and meal support block;

FIG. 12(a) is an SEM picture showing the fabricated probe used for the assembly of the zero-rise 3D array;

FIG. 12(b) is an enlarged SEM picture from FIG. 12(a);

FIG. 13(a) is an SEM picture showing the fabricated probe used for the characterization of high density tab bonding;

FIG. 13(b) is an enlarged SEM picture from FIG. 13(a);

FIG. 14(a) is an SEM picture showing the tip of the tab bonding tool having a 25 μm tip diameter;

FIG. 14(b) is an SEM picture showing the tip of the tab bonding tool having a 55 μm tip diameter with raised plus;

FIG. 14(c) is an SEM picture showing the tip of the tab bonding tool having a 60 μm square tip with raised plus;

FIG. 15(a) is an SEM picture showing the assembled and bonded probe with 25 μm wide tab (40 μm pitch);

FIGS. 15(b)-(c) are SEM pictures showing the assembled and bonded probe with 25 μm wide tab (40 μm pitch);

FIG. 16 is an SEM picture showing the assembled and bonded probe with 10 μm wide tab (15 μm pitch);

FIGS. 17 and 18(a)-(c) illustrate the zero-rise 3D array on a US penny or human finger;

FIG. 19(a) illustrates a cross-sectional view of traditional microsystems on a platform having components physically mounted on the platform with electrical wire bond connections, FIG. 19(b) illustrates a cross-sectional view of traditional microsystems on a platform having components recessed into a cavity with electrical wire bond connections FIG. 19(c) illustrates a cross-sectional view of traditional microsystems on a platform having components wherein the electrical connections use wire bonding from component pads to platform pads and routing lines patterned on the platform between components;

FIGS. 20(a)-(c) illustrate a series of views of traditional 64-channel integrated wireless microsystem on a silicon platform called SPIDER (Subcutaneous Programmable Interface Device for Extracellular Recording) measuring 1.4 cm×1.54 cm;

FIG. 21 illustrates a fully-implantable neural prosthetic microsystem;

FIG. 22(a) illustrates a cross-sectional view of the overlay cable according to the present disclosure;

FIG. 22(b) illustrates a top view of the overlay cable according to the present disclosure;

FIG. 22(c) illustrates a side view of the microsystem integration method using the overlay cable according to the present disclosure;

FIG. 22(d) illustrates an enlarged top view of the tab portion of the overlay cable according to the present disclosure;

FIGS. 23(a)-(d) is a series of views illustrating the microsystem integration using overlay cable approach, beginning with a platform with multiple components (FIG. 23(a)) and an overlay cable design (FIG. 23(b)), overlaying the cable overlay onto the platform and aligning and ultrasonically bonded to components on the platform (FIG. 23(c)), with an enlarged view of the metal tab of the overlay cable bonded to the pad on the component (FIG. 23(d));

FIG. 24 illustrates an overlay cable that can be wrapped around the platform for the double-sided integration of components;

FIG. 25(a) illustrates an SEM image of the parylene overlay cable;

FIG. 25(b) illustrates an SEM image of the tab and interconnect regions of the overlay cable;

FIG. 25(c) illustrates an SEM image of the tab and interconnect regions of the overlay cable;

FIG. 26(a) illustrates an SEM image of the front side probe array tabs and cutout regions in the overlay cable;

FIG. 26(b) illustrates an SEM image of the back side probe array tabs and cutout regions in the overlay cable;

FIG. 26(c) illustrates an SEM image of the front side circuit bonding tabs and cutout regions in the overlay cable;

FIG. 26(d) illustrates an SEM image of the back side circuit bonding tabs and cutout regions in the overlay cable;

FIGS. 27(a)-(b) illustrate photographs of the cable designed to connect the 3D array with the front-end signal conditioning chip;

FIGS. 28(a)-(b) illustrate photographs of the fabricated parylene overlay cable on a US penny;

FIG. 29 illustrates a neural recording microsystem front-end integrated using the compact 3D array and overlay cable approach of the present disclosure;

FIG. 30(a) illustrates a top view of a cavity formed in a platform;

FIG. 30(b) illustrates a cross-sectional view of the cavity of FIG. 30(a) taken along Line 30-30;

FIG. 30(c) illustrates a top view of a signal conditioning chip disposed in the cavity of the platform;

FIG. 31(a) illustrates a diagrammatic view of a probe tab bonding to platform pads;

FIG. 31(b) illustrates a diagrammatic view of a cable overlay with tab bonding to platform;

FIGS. 32(a)-(h) illustrate a series of photographs of tab bonding employing the present disclosure having a probe array with 25 µm wide tabs, a chip with 100 µm wide tabs and patterned interconnect lines being 10 µm wide; and FIG. 33 illustrates an integrated microsystem using the parylene overlay cable approach of the present disclosure.

DETAILED DESCRIPTION

The following description is merely exemplary in nature and is not intended to limit the present disclosure, application, or uses.

The Compact 3D Array: Concept and Design Considerations

A new high-yield compact approach to 3-D microelectrode array formation is described here along with its design considerations according to principles of the present teachings. In the present architecture, shown in at least FIGS. 3(a)-(c), a microsystem 2 is provided wherein the 2-D probes 10 (passive or active) are designed to eliminate the undesirable wide-span lateral wings used in the past, resulting in a more generic design that also saves layout area on the mask. Extending off the back end 12 of this 2-D probe design are bendable electroplated gold tabs 14 for lead transfer. The platform design relies on a thicker silicon substrate 16, rather than the thin boron diffused structure used in the past, to countersink the probe back end 12 into slots 18 formed in the silicon. As shown in FIG. 3, the platform slot is used to countersink the back end 12 of the 2-D probe 10 and hold it on an internal ledge 20 while the shanks 22 penetrate through the silicon substrate 16. Each of the shanks 22 includes a plurality of electrode sites 23 electrically coupled to each tab 14 via electrode leads 25 extending along shanks 22 (see FIGS. 3B and 6A).

The present architecture allows for a high degree of flexibility and control of design parameters. For any given geometric configuration of recording sites (as required by an application), the appropriate 2-D probes can be designed and then the platform can be designed to fit the probes at the appropriate spacing. As a key advantage, this architecture allows to further push the limits of device compactness. Consider the length and width of a slot in the platform. A single slot actually consists of a top-side slot, which countersinks the back end and creates a supporting ledge, and a back-side slot, which creates a through hole 24 for the shanks 22 together with the top-side slot 18 (refer to FIG. 3(b)). In this platform design, a single slot is preferred rather than perforated holes for each shank to simplify fabrication and assembly.

Figure 1A:
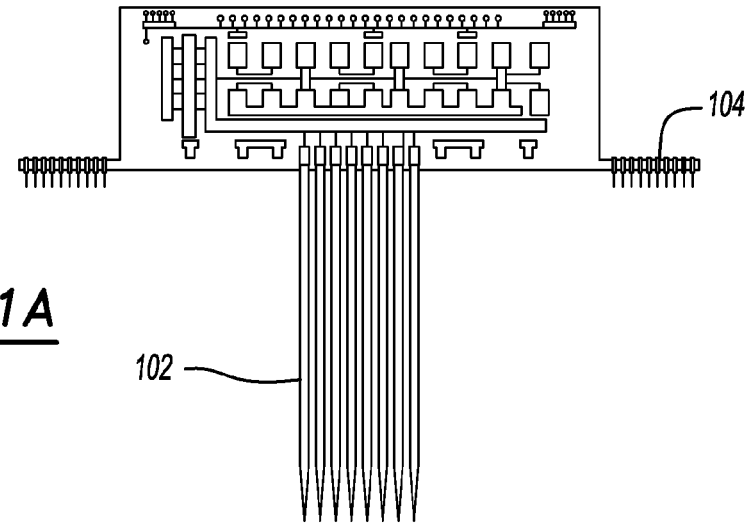
FIG. 1(a) illustrates an active probe designed for 3D assembly includes lateral wings and spacer slots on the back end according to the prior art.
Figure 1B:
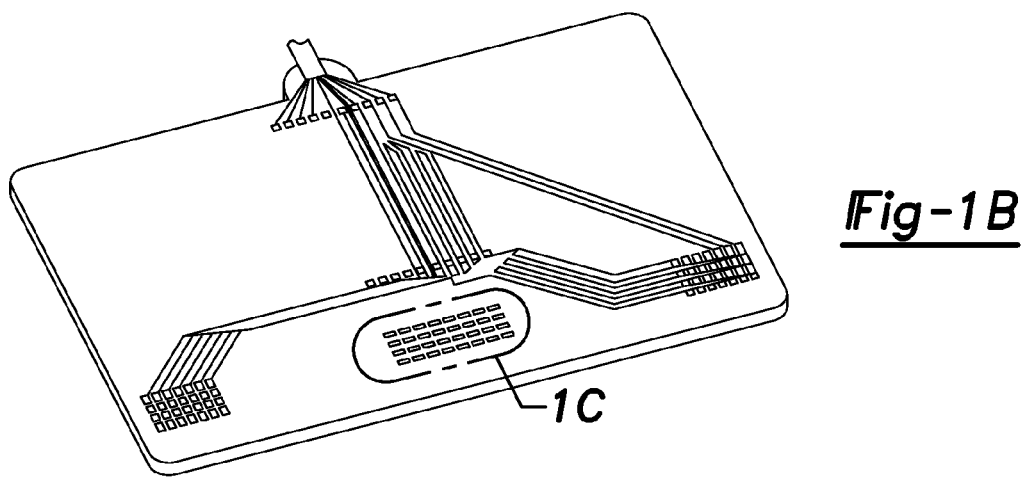
FIG. 1(b) illustrates an etch-stop defined silicon platform designed for assembly having individual holes for shanks and routing lines.
Figure 1C:
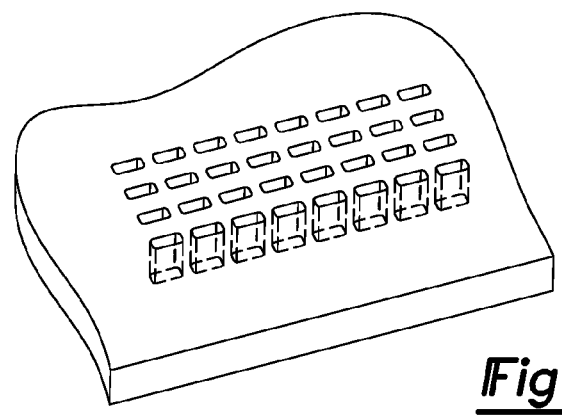
FIG. 1(c) illustrates an enlarged etch-stop defined silicon platform designed for assembly having individual holes for shanks and routing lines.
Figure 2A:
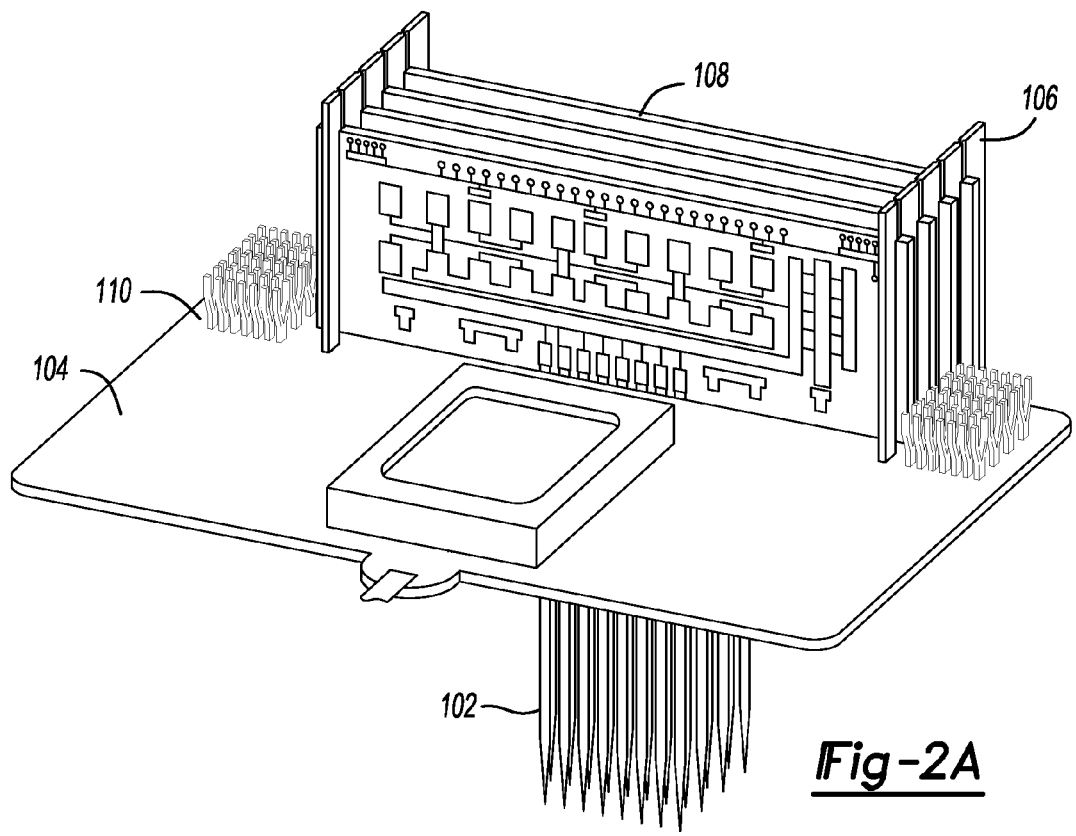
FIG. 2 illustrates an assembled 3D array using four parallel active probes orthogonally assembled on a silicon platform and stabilized with silicon spacers.
Figure 2B:
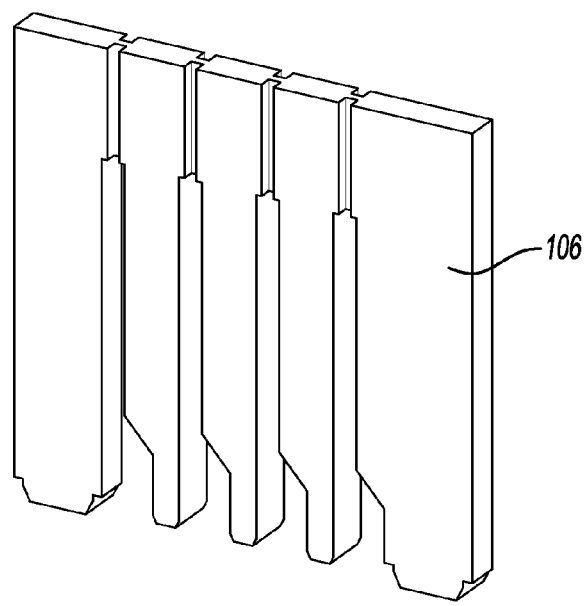
Figure 3A:
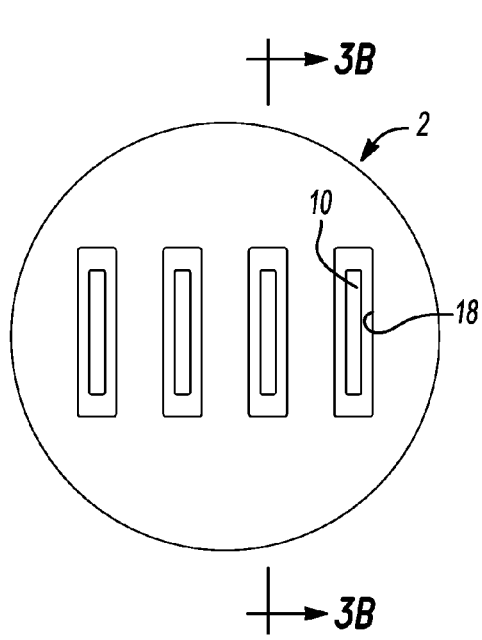
FIG. 3(a) illustrates a top view of a 3D array of neural microelectrodes according to the present disclosure.
Figure 3B:
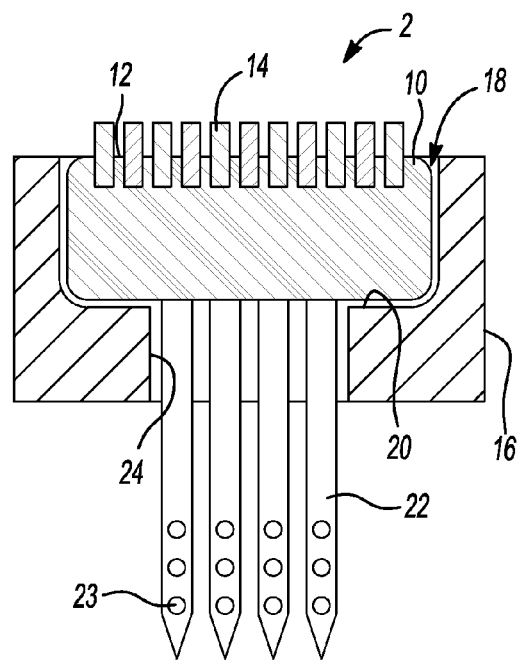
FIG. 3(b) illustrates a cross-sectional view of the 3D array of neural microelectrodes according to the present disclosure taken along lines 3-3 of FIG. 3(a)
Figure 3C:
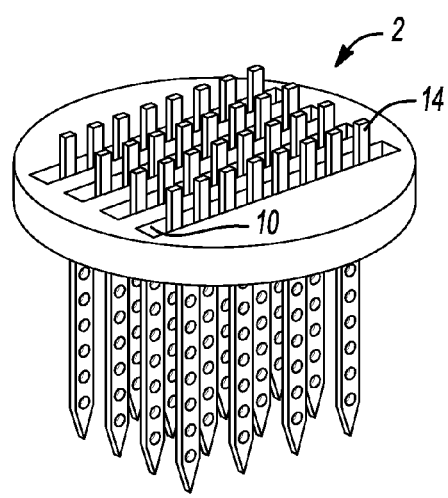
FIG. 3(c) illustrates a top perspective view of the 3D array of neural microelectrodes according to the present disclosure.
Figure 3D:
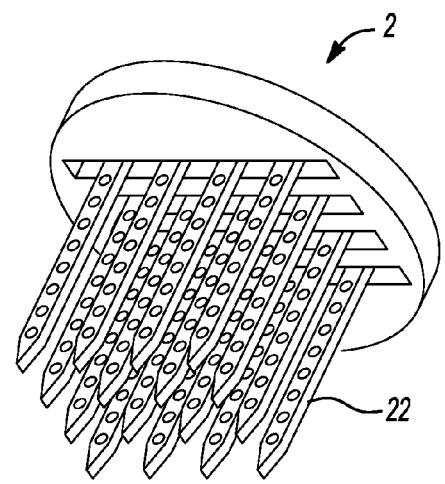
FIG. 3(d) illustrates a bottom perspective view of the 3D array of neural microelectrodes according to the present disclosure.
Figure 4:
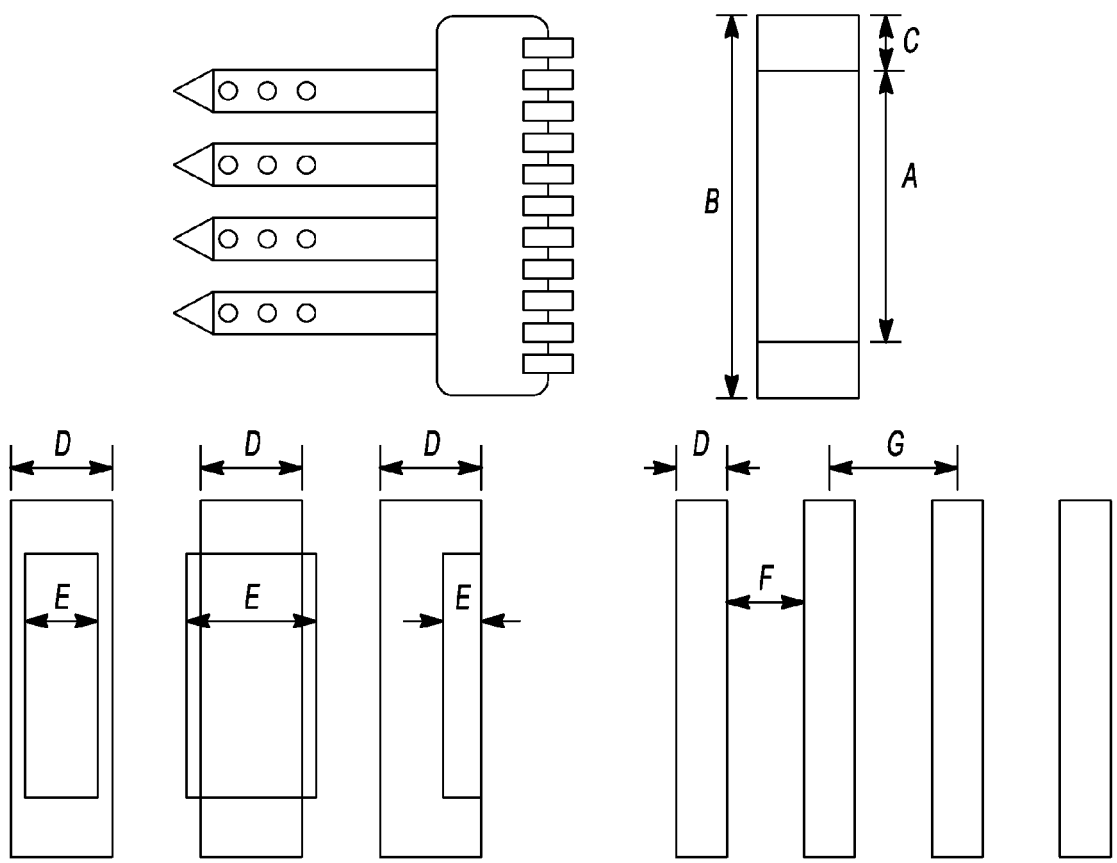
FIG. 4 is a series of views illustrating various slot design configurations for zero rise 3D neural probe arrays.

Referring to FIG. 4, the minimum back-side slot length, dimension A, is determined by the number of shanks, their width and pitch. For example, a 2-D array consisting of 4 shanks, each 50 µm wide separated by 150 µm, would span a total distance of 650 µm representative of a typical 2-D silicon neural recording array. Therefore, the minimum back-side slot length, dimension A in FIG. 4, would be 650 µm, not including any assembly tolerances. The minimum top-side slot length and the length of the probe back end, dimension B in FIG. 4, determine the overall size of the array and limited in minimum size by the span of the shanks. In this assembly approach, the back end of the probe must overhang the span of the shanks (dimension C in FIG. 4) to create wings that sit on a support ledge created in the platform. However, unlike the previous approach to wings which carried electrical leads and spanned hundreds of microns, here the wings are used purely for physical support, so this dimension is only on the order of tens of microns. It should be appreciated that the wings could be eliminated depending on the specific application and use.

The slot width is determined by the thickness of the probe. For passive probes, the thickness of the back end and shanks will differ only by a few microns where the difference is determined by the thickness of the gold electro-plated tabs. For active probes, the thickness of the back end is approximately 3 times larger (~50 µm) compared to the shank thickness (~12-15 µm). The typical back end and shank thicknesses for the University of Michigan passive and active silicon probes are detailed in Table 1. The minimum top-side slot width, dimension D in FIG. 4, is determined by the total thickness of the back end of the probe, while the minimum back-side slot width, dimension E in FIG. 4, is determined by the thickness of the shanks. Since the probe is countersunk into the platform from the top-side, a natural stabilization mechanism is created but due to finite assembly tolerances, this dimension also determines the tipping angle of the shanks. For example, a 5 µm assembly tolerance in the top-side slot would result in a 1° tipping angle of the shanks when the back end is placed in a 300 µm deep slot. The back-side slot primarily creates a through hole for the shanks and is not critical in stabilizing the probe. For passive probes it is acceptable for the top- and back-side slot widths to be equal but in practice (during fabrication) there will be a mismatch due to mask alignment tolerances on the order of 1 µm. Therefore, it is preferred that the back-side slot be wider than the top-side slot so that in the case of misalignment no obstruction is created in the through hole, making the assembly easier. In the case of 3-D arrays using active probes, slot width and alignment should be designed appropriately such that the back-side slot is offset from the top-side slot to achieve the best stabilization mechanism.

TABLE 1

Shank and back end thicknesses for passive and active probes.

| | | | Passive Probe | Active Probe |
|---|---|---|---|---|
| A. | Silicon back end | | 12 µm | 50 µm |
| B. | Silicon shank | | 12 µm | 12 µm |
| C. | Lower dielectric stack | | 0.9 µm | 0.9 µm |
| | Pad oxide (thermal) | 1500 Å | | |
| | LPCVD oxide | 3000 Å | | |
| | LPCVD nitride | 1500 Å | | |
| | LPCVD oxide | 3000 Å | | |
| D. | Polysilicon | | 0.6 µm | 0.6 µm |

TABLE 1-continued

Shank and back end thicknesses for passive and active probes.

| | | | Passive Probe | Active Probe |
|---|---|---|---|---|
| E. | Upper dielectric stack | | 0.9 μm | 0.9 μm |
| | Pad oxide (thermal) | 1500 Å | | |
| | LPCVD oxide | 3000 Å | | |
| | LPCVD nitride | 1500 Å | | |
| | LPCVD oxide | 3000 Å | | |
| F. | Site metallization | | 0.35 μm | 0.35 μm |
| | Titanium (Ti) | 500 Å | | |
| | Iridium (Ir) | 3000 Å | | |
| G. | Bond pad metallization | | 0.55 μm | 0.55 μm |
| | Chromium (Cr) | 500 Å | | |
| | Gold (Au) | 5000 Å | | |
| H. | LTO passivation | | — | 1 μm |
| I. | Gold shield | | — | 0.5 μm |
| J. | Gold plated beam lead tabs | | 5 μm | 5 μm |
| Shank thickness: | | | B + C + D + E + F = 14.75 μm | B + C + D + E + F = 14.75 μm |
| Back end thickness: | | | A + C + D + E + G + J = 19.95 μm | A + C + D + E + G + H + I + J = 59.45 μm |

The spacing between slots, dimension F in FIG. 4, is determined by the array pitch (dimension G). Typically, shanks are spaced 100-200 μm apart depending on the cell sizes in the specific region of interest to allow the array to record from virtually all neurons in a given area. This dimension determines the maximum length of the bond tabs on the probe while the thickness of the tabs is a fabrication process parameter (typically 3-5 μm thick) which determines the bending strength. The maximum tab length, dimension F in FIG. 4, is the difference between the array pitch (dimension G) and the top-side slot width (dimension D). The maximum width and pitch of each tab on the probe is determined by the number of sites and the total length of the probe back end. Consider a 16 site 2-D array with 4 shanks spanning 650 μm. If the extension of the back end is 50 μm on each side resulting in a total span of 750 μm for the back end, the tab pitch would be approximately 45 μm. Since these tabs are intended to be ultrasonically bonded to pads on the platform and therefore do not have the same minimum size requirements as would wire-bonded tabs, the maximum width of each tab is determined by the minimum gap between two tabs which is only limited by the fabrication tolerance to avoid electrical shorting. In fact, tab bonding allows for much smaller and tighter tab designs compared to wire bonding, so it is not necessary to utilize the full span of the back end for the tab design. This allows the tab size and pitch to be optimized depending on bonding and/or interface requirements. A design with narrow closely-spaced tabs could facilitate the assembly process by allowing a single ultrasonic bond simultaneously across all tabs. Also, in this 3-D array formation, routing lines on the platform are not considered to be a limitation on the minimum spacing between slots (dimension F) because a planar array of bond tabs is created which opens several options for microsystem integration not previously possible. One such approach is to use flip-chip bonding technology, as is, in fact, being developed for the Utah microelectrode array. The approach taken in the present work uses an overlay film carrying the interconnect lines directly on top of the array and bond pads as will be discussed herein.

Figure 5:
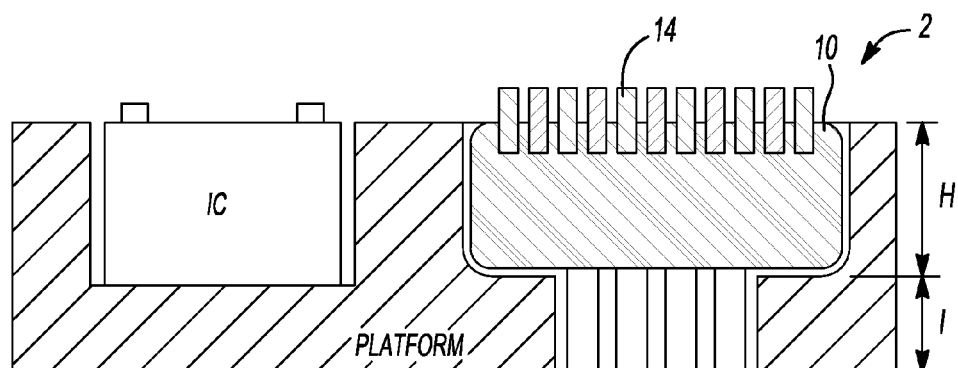
FIG. 5 illustrates a cross-sectional view of the 3D array of neural microelectrodes according to the present disclosure.

Consider now the thickness of the platform. A standard silicon wafer, which measures approximately 500 μm in thickness, is convenient for processing and results in a corresponding 500 μm of vertical rise above the cortical surface when the array is implanted. Thinner platforms could be considered for the design, to be determined from the trade-off between vertical rise and mechanical robustness. In the present work, the standard silicon wafer thickness was used for the platform design because it is not only strong enough to handle during bonding and implantation but is also compatible with countersinking integrated circuit chips, creating a robust package for a microsystem containing the 3-D array integrated with electronics. The top-side and back-side slot depths, dimensions H and I in FIG. 5, are determined by the height of the back end of the probe such that it sits flush with the top surface of the platform when inserted. For passive probes, the minimum height of the back end is limited by the fan out of the leads connecting the sites to the tabs. In 3 μm technology, a passive probe having 16 sites would require a minimum H of approximately 50 μm for the lead fan out at the back end (eight 6 μm pitch lines). Adding some overlap of the tabs onto the back end, this passive probe could be realistically designed having a back end height of about 75 μm, which would also be the depth of the top-side slot (dimension H), leaving 425 μm for the backside slot depth (dimension I). Active probes with circuitry integrated on the back end typically have much taller back ends, depending on the complexity of the circuitry. For example, a multiplexed (64:8) recording probe with 8 amplifiers measures approximately 2.5 mm tall when fabricated in the 3 μm active probe process. In some embodiments, the back end of active probes is limited to the thickness of the platform by including only the site selection circuitry, and that the remaining signal conditioning circuitry is designed as an ASIC that would be integrated into the platform as shown in FIG. 5. Alternatively, a "hybrid" active probe could be created by designing a chip that makes use of the smaller-feature technologies available at foundries and mounting this chip to the back end of a passive probe, as in the case of the hybrid flip-chip bonded cochlear array. These "hybrid" active depth probes could then be assembled into a 3-D array with the appropriately designed platform.

Figure 6A:
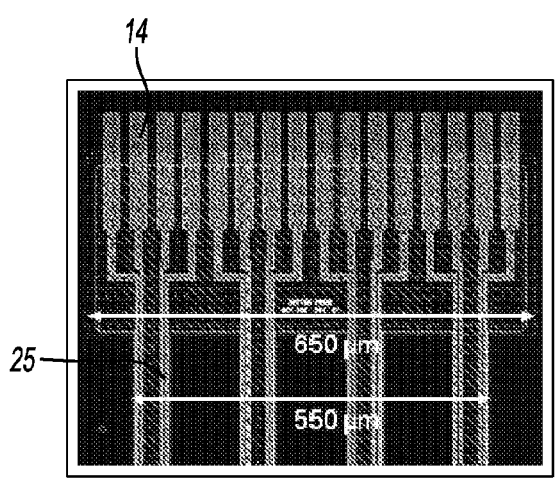
FIG. 6(a) illustrates a silicon neural probe design.
Figure 6B:
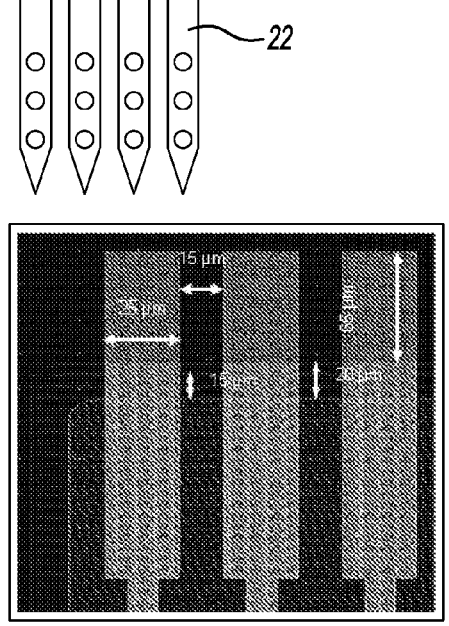
FIG. 6(b) illustrates an enlarged view of the silicon neural probe design of FIG. 6(a)
Figure 6C:
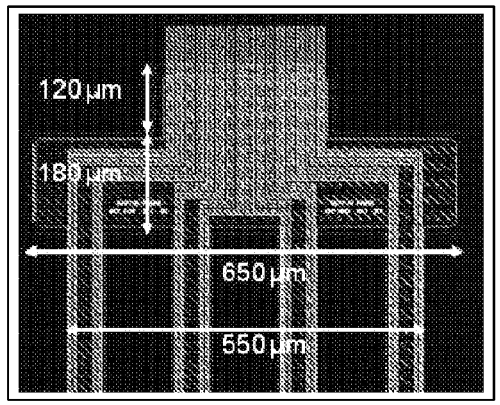
FIG. 6(c) illustrates a high-density silicon neural probe design.
Figure 6D:
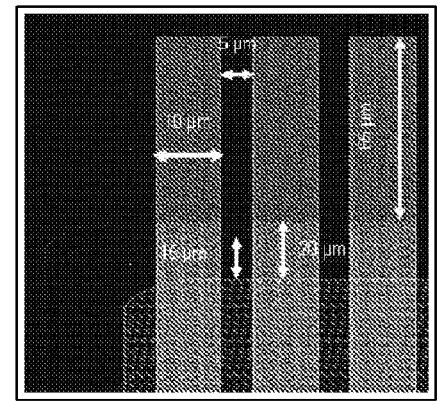
FIG. 6(d) illustrates an enlarged view of the high-density silicon neural probe design of FIG. 6(c)
Figure 7A:
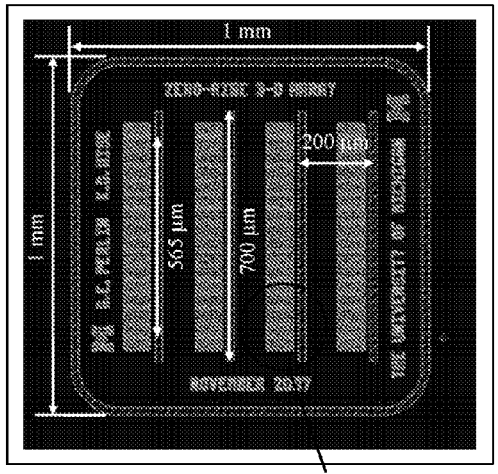
FIG. 7(a) illustrates a platform design for a compact 3D neural probe array.
Figure 7C:
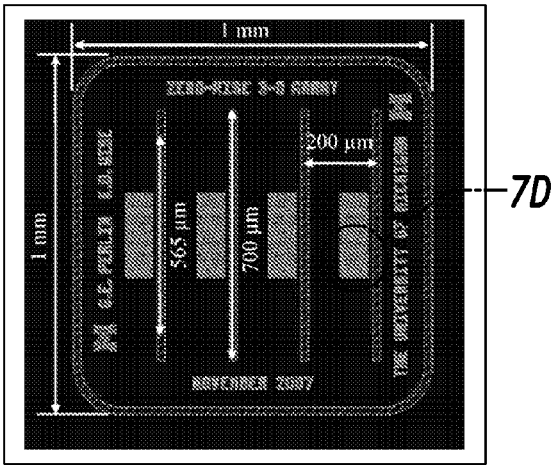
FIG. 7(c) illustrates a high-density compact 3D neural probe array.
Figure 7B:
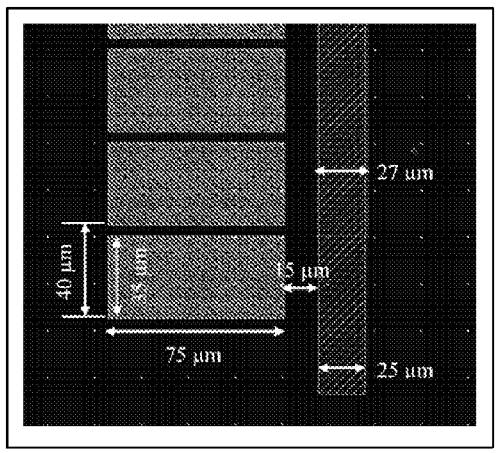
FIG. 7(b) illustrates an enlarged view of the compact 3D neural probe array of FIG. 7(a)
Figure 7D:
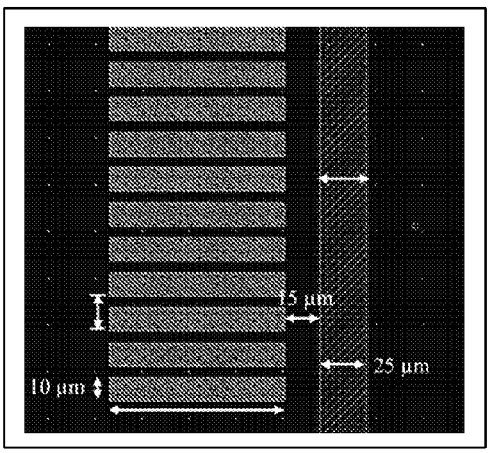
FIG. 7(d) illustrates an enlarged view of the high-density compact 3D neural probe array of FIG. 7(c)

In this work, two 16 channel (4 sites per shank) probe designs are considered. The difference is only in the bond tab design at the back end. The first design is a typical probe where the tab width is maximized to utilize the entire span of the back end. In the second design, a smaller tab with tighter pitch is investigated to explore bonding feasibility. The high-density tab design can provide useful information for future designs of probes that include more sites or channels (in the case of active probes requiring power and control lines) in a limited space. These two probe designs are shown in FIGS. 6(a)-(d) along with the overall dimensions. In both designs, four shanks span 540 μm. Each shank is 60 μm wide (including boron diffusion), leaving a 100 μm gap between shanks. With a 50 μm ledge on each side, the total width of the back end is 650 μm. Note that as shown in the detail of FIG. 6, this 650 μm width includes boron lateral diffusion (typically 55% of the diffusion depth for wide mask openings) and a dielectric overlap to prevent leads shorting to the platform. The probe with the larger tab design is shown in FIG. 6(a) and has 16 tabs spaced at a 40 μm pitch, each tab being 25 μm in width. The probe with a high-density tab design also includes 16 tabs but has a 15 μm pitch with 10 μm wide tabs as shown in FIG. 6(c). In fact, at this pitch, approximately 42 tabs can be accommodated given the span of the back end on this typical four shank probe although only 16 have been included here for testing the bonding feasibility. The corresponding platform designs for these probes are shown in FIG. 7. The top-side slot width is designed to be 25 μm based on both the typical probe fabrication process given in Table 1 and includes assembly tolerances. The back-side slot width is made wider than the top side slot by an alignment tolerance of 1 μm resulting in a slot width of 27 μm. In designing the top side slot length, a 25 μm assembly tolerance was used on each side, so that the total top side slot length is 700 μm. The top-side slot depth and the height of the passive probe back end in this work was chosen to be 300 μm leaving about 200 μm for the back-side slot depth need to create a through hole for the shanks. Although the back end could have been designed much smaller, a taller back end was designed to demonstrate the feasibility of deep slots as would be required by active probes. The platform extends the slots by 150μm on all sides to facilitate assembly and handling, resulting in a 1 mm2 device. These platforms are designed to hold four probes spaced 200 μm apart, demonstrating a 64-channel array (4×4×4) to interface with neurons in a 1 mm3 volume of tissue.

Fabrication and Assembly
Platform Fabrication

The fabrication of the passive and active 2-D silicon arrays is a standard process, the details of which can be found elsewhere. The focus here is on the fabrication of the platform. The fabrication of the platform starts with a double-side-polished silicon wafer, approximately 500 μm thick. First, silicon dioxide is grown on the wafer using thermal oxidation at 1100° C. to obtain an oxide thickness of approximately 1.2 μm. Next, the front-side of the wafer is metalized with 200 Å of chromium (Cr) and 5000 Å of gold (Au) and patterned using liftoff to define bond pads on the platform. Continuing processing on the front-side of the wafer, slot openings and the perimeter of the platform are defined in a single lithography step using a thick photoresist (~15 μm). Anisotropic deep reactive ion etching (DRIE), a combination of silicon etching and pasivation, is used to etch the patterned areas approximately 300 μm deep from the front-side of the wafer. Following this step, the process wafer is mounted to a glass carrier wafer using photoresist. Then the back side of the process wafer is aligned to the front side and patterned to define the back-side slot and perimeter regions. Again, anisotropic DRIE is used to etch the patterned regions to a depth of about 200 μm until the back side etch reaches the front-side etch, creating a through hole in the slot regions and releasing the platform from the bulk wafer in the perimeter. Finally, the process wafer is soaked in acetone to dissolve the photoresist and separate the individual platforms from the carrier wafer. An isopropyl alcohol (IPA) rinse is used to clean any remaining residue from the devices.

Simultaneous etching of the slots and perimeter, shown in FIG. 8 as captured by an optical profilometer (Zygo), simplifies the fabrication process into just three lithography steps; bond pad patterning, front-side slot/perimeter etch, and back-side slot/perimeter etch and release. The etch rate was characterized for the platform design shown in FIG. 7 using a high-aspect-ratio etch recipe with 130 sccm of SF6 for silicon etching and 85 sccm of C4F8 for the passivation step with a chamber pressure of 94 mT and a platen power of 100 W. It is well known in DRIE etching that the etch rate decreases for deeper structures so the average etch rate is given here. Using the above mentioned recipe, the characterized etch rate for a 300 μm deep slot/perimeter with an opening of 25 μm is approximately 1.6 μm/min. The etch rate is only slightly faster, 1.9 μm/min, for the 200 μm deep back side etch with approximately the same mask opening. In FIG. 9 the profile of slots etched 300 μm deep is shown in an SEM picture. The taper towards the bottom of the slot was calculated to be approximately 2° from measurements taken from this cross-section in the SEM. The key in this process is to ensure that a through hole is created in the slot region before the device is released along the perimeter. This can be achieved by designing the two openings to be equally wide. A cross-section of the etched slots, shown in the SEM picture of FIG. 10, reveals a cusp that is formed at the point where the back-side slot meets the front-side slot. Although the opening at the meeting point is wide enough to insert the shanks, this cusp can hinder the insertion of shanks if the design tolerance is too tight. This can be overcome by designing the back-side perimeter opening to be slightly smaller (~5 μm) in width compared to the slot opening. This allows the back-side slot area to be over etched before the perimeter is released, thus creating a smoother through hole in the shank penetration region.

Assembly

The released platforms, measuring 1 mm×1 mm×0.5 mm must be secured during the assembly procedure, which includes the insertion of 2-D probes into the platform followed by tab bonding to make electrical connections from the probe to the platform. To secure these platforms, an assembly wafer was micromachined using a two-mask DRIE process. In the first step, the outline of the platform is etched approximately 200 μm deep. Then a second DRIE etch from the backside of the wafer was used to produce a single through-hole overlapping all slot regions. The wafer was then diced into approximately 1 cm×1 cm dies of silicon (500 μm thick) containing multiple micro-machined mounting regions, referred here as the silicon assembly carrier. Since the assembly carrier is only 0.5 mm thick, a supporting metal block 5 mm tall was used to clear the shank length (4 mm in this work) during assembly. The silicon carrier is secured to the support block using a silicone elastomer around the edges, creating the assembly jig shown in FIGS. 11(a)-(c). The 3-D array platform is placed in the carrier wafer and secured by applying a dissolvable lacquer such as nail polish or hand soap along the perimeter of the platform and allowing it to harden in place. Care must be taken to avoid drowning the entire platform in the lacquer and also to prevent the lacquer from encompassing the bond pads on the surface of the platform. Since the silicon carrier is micromachined, multiple platforms can be assembled simultaneously using this setup. Using this jig, a three-way micromanipulator mounted with a vacuum pick, and a stereo-microscope, individual 2-D probes are aligned to the slots in the platform and dropped into place. Following the insertion of all 2-D probes (four probes in this work), a glass micropipette or tweezers can be used to roll over the platform, simultaneously bending all tabs onto the bond pads on the platform. Each array should be positioned in the slot such that the probe sites face toward the bond pads on the platform. This ensures that the tabs, which have a chromium adhesion layer on the back side, are bent over with the gold side down onto the bond pads on the platform. The jig is then moved to a wire bonder to make electrical connections using ultrasonic tab bonding of the gold tabs to the gold bond pads. The entire assembly process from inserting four 2-D arrays to bonding 64 tabs, takes less then half and hour for a single device. In comparison, the previous approach used to assemble a similar-sized array, involving the alignment of individual shanks to corresponding holes and the insertion of spacers took more than 3 hours. Once bonding and electrical continuity tests have been completed, the loaded platform can be soaked in acetone or water, depending on which lacquer was used, for approximately 10 minutes and removed with tweezers from the jig.

The fabricated probe designs used for assembly in this work are shown in the SEM pictures of FIG. 12 and FIG. 13 along with a close up of the electroplated gold tabs. Custom tab bonding tools, shown in FIG. 16, were ordered from Gaiser Tool Company with various tip configurations to investigate single- and multi-tab bonding feasibility. One of these has a flat tip with a 25 μm diameter while the other two are larger in size (55 μm and 60 μm) and have a cross ridge pattern at the tip. The patterned tips are thought to be more efficient in the transfer of ultrasonic energy, making a stronger better-quality bond. SEM images of an assembled and bonded probe with 25 μm and 10 μm wide tabs are shown in FIGS. 14 and 15 using the K & S model 4123 bonder with experimentally-determined parameter settings. The wider tabs were ultrasonically bonded using the 25 μm diameter flat tip (FIG. 14(*a*)). The high-density tabs were bonded using the larger bonding tools with the square and round tips to demonstrate simultaneous multi-tab bonding. These tools were used to bond two 25 μm wide tabs and four high-density tabs with 15 μm pitch simultaneously, demonstrating the ability to speed up the assembly process. The bond quality depends on three main parameters of the ultrasonic bonder: the force exerted by the wedge, the power of the ultrasonic waves, and the duration of the process. Electrical continuity was verified between the bond pads on the platform and the sites on the probe by dipping the shanks into saline solution connected to an electrode and probing the bond pad on the platform. A photograph of the fully-assembled compact 3-D array with the platform measuring 1 mm×1 mm holding 4 mm-long shanks is shown on a U.S. penny in FIG. 17. This array has 64 sites using four probes in parallel with each having 4 shanks and provides an electrical interface covering approximately 1 mm3 in tissue. Other highlight views of the array or shown in the photographs of FIG. 18.

Discussion

A novel approach to the formation of 3-D arrays of neural electrodes was presented herein. The key advantages of this approach include (1) a low-profile nature that facilitates implantation, (2) alternative options of system integration including flip-chip bonding given the planar surface, (3) compactness, and (4) ease of assembly and robustness. However, the arrays by themselves are limited in use; bonding individual wire connections to the outside world is tedious and inconvenient. At the least, a micro-fabricated cable is necessary but due of the nature of the neural signals, buffering/amplification is critical up-front for transferring uncorrupted data out of the implant. Several options are available for electrically integrating this array with signal conditioning circuitry, including flip-chip bonding of an ASIC onto the array (vertical integration) as done with the Utah array. However this approach results in a stacked structure that ultimately defies the low-profile nature of this architecture. Previous Michigan 3-D arrays used lateral integration with circuit chips placed on the same platform as the 3-D array of probes. However the lateral routing of leads from the probes to the chips consumed significant area on the platform, and was partly a limitation on the minimum size of the array (the other limitation is due to the lead transfers from lateral wings). Even when active probes are used, routing of leads to an integrated silicon cable consumes significant lateral area on the platform. In this work, the footprint of the array is designed to be the minimum size possible (limited by the span of the shanks). With this constraint and taking advantage of the zero-rise, a lateral integration approach that uses a flexible overlay cable is presented herein.

Microsystem Integration

Neural probes are the fundamental components upon which implantable wireless neural recording/stimulating microsystems are built. In addition to the sensor, Microsystems integrated circuit chips and other hybrid parts such as a coil antenna are needed. The required components must be both physically and electrically integrated to produce a viable microsystem. Typically, a substrate such as a silicon platform is used because it can serve both purposes. Components, such as those referenced at components 130 and 132 (FIGS. 19(*a*)-(*c*)), can be attached to or recessed into the silicon 134 while electrical routing 136 between components can be lithographically patterned on the surface 142 of the platform 134 as shown in FIG. 19(*a*) and 19(*b*). Wire bonding is used to make electrical connections between the pads 138 on the components 130, 132 and pads 140 on the platform surface 134, as shown in FIG. 19(*c*). The drawbacks of this method include: (1) the surface area required to route the platform interconnections around the components becomes significant as the number of components or the channel-count of the microsystem increases, and (2) wire bonding adds vertical height to the system and requires a finite lateral spacing between two bonding pads (the pitch) and between the component bonding pad and platform bonding pad.

Consider the 64-channel neural recording microsystem developed prior to this work, which uses the conventional system integration method just described. SPIDER (Subcutaneous Programmable Interface Device for Extracellular Recording) is shown in FIGS. 20(*a*)-(*c*). It includes two 132-channel silicon electrode arrays, four 16-channel front-end integrated circuit chips, two 32-channel signal processing chips, a wireless interface chip, a coil antenna and several surface mount (SMD) capacitors and inductors used for the wireless link. A silicon platform was designed and fabricated to physically assemble and electrically integrate the various components of this microsystem. First, photolithographically-patterned interconnects and bonding pads are defined using a single metal layer (Cr/Au, 200 Å/5000 Å) on an oxidized wafer. To achieve a low vertical profile, component recesses are formed using dry etching (~300 μm deep) so that each component can be embedded to sit flush with the top surface of the platform. The platform is released from the wafer using two-sided dry etching of silicon along its perimeter. Smooth rounded corners can be formed using a perimeter etch rather than simply dicing the wafer into squares. The fully populated and bonded platform is shown in FIG. 20(*a*). As shown in FIG. 20(*a*), the neural recording probes are integrated on the platform using a long silicon cable that extends laterally from the platform. The numerous bonding wires can also be seen in FIG. 20(*a*). This microsystem measures 1.4 cm×1.54 cm, and weighs 275 mg (populated).

This integration method is simple and straightforward but has many limitations. First, the probes are separated from the signal conditioning circuitry by long cables (1 cm-2 cm) that are monolithically integrated with the probe back end. In this application where microvolt signals are being transferred from tissue to the microsystem, noise corruption is of significant concern. The signal conditioning circuitry should be as close to the probes as possible. The cable, directly attached to the probe back end as in this method, exerts a tethering force on the probe and may cause it to be displaced from the target region of tissue and/or cause inflammation of the surrounding tissue due to micromotion of the brain in freely moving subjects. Second, for a complex high-channel count system such as this, the platform becomes relatively large due to the number of components, the routing lines, and bonding pads. For the 64-channel neural recording microsystem shown in FIGS. 20(*a*)-(*c*), 48% of the total platform area is consumed by the routing lines, bonding pads, component-to-bonding pad separation and bonding pad pitch. Not only do the routing lines and bonding pads consume significant area on the platform, they also become challenging to place such that there is a one-to-one correspondence between bonding pads of different components. For a complex multi-component microsystem such as this, using a single-metal interconnect level requires wirebond crossovers to form the necessary electrical connections. Criss-crossing wirebonds can results in low yield. A multi-level interconnect process is an option for the platform fabrication but becomes complicated and does not necessarily overcome the problem of area consumption. Furthermore, wirebonds are fragile and have a finite loop height, from as low as 50 μm for the shortest wires to more than 400 μm for the longest wires, adding vertical rise to the microsystem. Third, in this particular application, it is preferred to separate the front-end, where microvolt level analog signals are sensed and processed, from the electromagnetic interference of the wireless link, a challenge not insignificant with the stacked flip-chip approach. Minimizing the size of the front-end also allows for full implantation while the rest of the electronics package can be placed under the skin rather than directly on top of the implantation site as shown in the conceptualization of such an implant in FIG. 21.

Clearly, this microsystem, in particular, would benefit from a more compact and robust integration method that also allows for design flexibility. Three dimensional integration techniques using flip-chip bonding or through wafer interconnect technology are a possibility, but some applications especially the neural implants, require very low vertical rise to facilitate the post-surgical procedure of re-sealing the implant opening. This disclosure presents an alternative approach to microsystem integration that allows components to be closely spaced and eliminates the need for wire bonding.

A Compact Zero-Rise Integration Approach

In the present integration approach, a silicon platform is still used, but serves simply as a physical support for the various microsystem components. Although any rigid substrate can serve this purpose, silicon is still preferred so that lithographically-defined and dry-etched recesses can be easily formed to embed the components flush with the surface of the platform. The electrical connections between components are carried by a flexible overlay cable rather than routing on the platform. A conceptual picture of this integration method using a silicon platform and overlay cable is shown in FIGS. 22(a)-(d). The cable 30 is in the form of lithographically-patterned lines of metal 32 sandwiched between two layers of any polymer 34, 36 (ex. polyimide, parylene, SU8) which is compatible with semiconductor manufacturing techniques as conceptualized in FIG. 22(a). For implantable applications the polymer should also be biocompatible. Each end 38 of the cable 30 has cutouts 40 in the top 34 and bottom 36 polymer layers such that the metal lines 32 terminate as floating tabs 42 as shown in FIGS. 22(b) and 22(d). The flexible nature of the overlay cable 30 allows it to conform to the surface topology on the component 44 itself or between components 44, 46 as shown in FIG. 22(c). The electrical integration of the microsystem is achieved by aligning the overlay cable 30 on top of the components 44, 46, which are supported by the platform 48, and ultrasonically bonding, at 52, the cable termination tabs 42 to the component bonding pad 50 as shown in FIGS. 23(a)-(d).

The benefits of this integration approach are numerous. First, the choice of substrates for physical support of the components is flexible (ex. silicon, glass, ceramic, plastic) and depend on the application of the microsystem. Second, the area of the microsystem can be minimized by placing components within tens of micrometers from each other since electrical leads no longer need to be routed on the platform around the components. The area on top of components can be utilized for routing since the overlay cable is insulated on the top and bottom. This saves significant lateral space since the components can be placed much closer to each other and arranged more efficiently compared to the traditional method where electrical routing determines the lateral space and component arrangement (i.e., that needed for bonding from one component to the platform and from the platform to another component). Third, since wire is not involved in the bonding process, the tab pitch can be much smaller and multiple tabs can be bonded simultaneously, making assembly faster and more efficient. Furthermore, with the elimination of wire bonds, several cables can be stacked and oriented individually as needed. Stacked cable interconnects oriented independently offer design flexibility and simplicity in a small area with insignificant vertical cost since the thickness of the cable is only on the order of a few micrometers. It is worth noting that individually stacked cables are simpler to fabricate than a single cable with multiple metal layers due to planarization problems associated with lithography, especially beyond two or three layers. Fourth, the cable is not limited to the surface of the platform. It can be extended much longer to terminate in a connector or printed circuit board, for example. It can also be bent around the side of the platform to connect to components mounted on the other face as shown in FIG. 24. In some cases, this circumvents the need for more complex through-wafer interconnect technology needed for compact microsystem integration.

Overlay Cable Fabrication

The overlay cable is a sheet of polymer carrying metal traces that are insulated above and below. Parylene-C was selected as the structural material for the fabrication of these cables due to its compatibility with low temperature deposition, lithographic patterning, mechanical flexibility and biocompatibility. Fabrication begins with a silicon wafer having a sacrificial layer on the processing side. In this work, three sacrificial layers were explored: PECVD oxide (5000 Å), evaporated titanium (300 Å) and native oxide on bare silicon. Next, the first layer of parylene is deposited at room temperature using a Specialty Coating System PDS 2010. The deposition of parylene occurs on both sides of the wafer at an average thickness of 0.45 μm per gram of dimer. Approximately 5 μm of parylene is deposited but the precise thickness of the film is not a critical parameter. At least a few microns should be deposited since it acts as a structural layer. This layer of parylene is patterned using thick photoresist and dry etched in an oxygen plasma (100 sccm, 100 mTorr, 105W) to define the outline of the cable and tab cutout regions. The etch rate of parylene under these conditions, determined experimentally, is approximately 1600 Å/min. Following the parylene patterning, the interconnect lithography and definition take place. For the interconnect metal, a chromium (300 Å), gold (3500 Å), chromium (300 Å) stack is used and defined using liftoff. A top layer of chromium is used since a second layer of parylene will be later deposited, which has better adhesion to chromium than to gold. The next step is to open the tab regions with lithography and sputter an electroplating seed layer: Cr (300 Å), Au (2000 Å). Due to the 5 μm step height between the wafer and top surface of the parylene, it is critical that sputter metallization, due to its conformal coverage, rather than evaporation is used to deposit an electrically continuous seed layer. For the same reason, the tab regions and the interconnect metallization are defined in two steps rather than one. A single-step metallization will result in poor lithography near the edge of the step. After the deposition of the seed layer, lithography is again used to open the tab regions for electroplating. Before electroplating, an oxygen plasma ash (250 mT, 250 W, 1 min) is used to modify the resist surface so that it is hydrophilic to avoid wetting voids in the electroplating solution. The tab regions are then electroplated with gold at a current density of 3 mA/cm2 to a thickness of 4.5 μm to 5 μm. The electroplating resist is stripped in acetone along with the liftoff of the seed layer. The top parylene layer is deposited (~5 μm), similar to the first layer, patterned and dry etched in the field and tab regions. The final step is to release the individual cables from the wafer. As mentioned, three different sacrificial layers were explored (PECVD oxide: 5000 Å, Ti: 300 Å, native oxide on silicon: 10 Å-20 Å) as well as parylene deposition with and without adhesion promoter (2.5 mi A-174 silane, 250 mi IPA, 250 mi DI H2O). These wafers were successfully released in 1:1 HF:DI H2O. The PECVD oxide sacrificial layer was not only the longest release method (overnight) but also caused the cables to stick to the wafer even after all oxide had been undercut in the HF solution, causing low yield. Using a thin titanium sacrificial layer or bare silicon provides the quickest release (~30 min) and highest yield. Obviously, using adhesion promoter in the deposition of the first parylene layer makes it more difficult to release the cables, requiring significant agitation. In this fabrication sequence it was found that adhesion promoter is not critical since contact lithography was successful without significant peeling or bubbling of the parylene layer.

The details of a released parylene cable 30 are shown in the SEM images of FIG. 25. The tabs 42 overlaying the IC are 75 µm wide and the parylene cutout region 40 is 100 µm on each side, leaving about a 12 µm gap on three sides of the tab. The back side of the cable 30 in the tab regions overlaying the 3-D probe array is shown in the SEM images of FIGS. 26(a)-(d). As shown in FIG. 26(d), there remains a thin chromium layer 54 (from the seed layer deposition) on the back side of all tabs 42 after cable release. Chromium cannot be ultrasonically bonded to gold pads, so the cable should be overlaid on the microsystem components with the gold electroplated side facing down. Mask design and fabrication should also account for this packaging requirement. Alternatively, each cable would need to be individually etched in a chromium etchant, which is tedious and not recommended. Photographs of a fabricated parylene cable highlighting the flexibility and scale of the structure are shown in FIGS. 27(a)-(b) and 28(a)-(b).

Neural Microsystem Assembly and Integration

The microsystem integration method described thus far using the overlay cable approach has been applied to integrate the front-end of a neural recording microsystem. As described in the present disclosure, the front-end of the neural recording microsystem includes the electrode array and the signal conditioning chip. Recall that it is critical for the signal conditioning circuitry to be as close to the recording sites as possible so that the microvolt signals are not corrupted by noise or leakage, while the rest of the system circuitry can be placed at a distance. To integrate this microsystem a silicon package and overlay cable were designed. This package can hold a 64-channel 3-D array of 4 neural probes using and a 16 channel signal conditioning chip. Although there are 64 available sites, the parylene overlay cable designed in this work is used to transfer only 16 of the 64 channels for demonstrating this integration approach. Active probes capable of site selection of 16 out of 64 channels could easily replace the passive probes. Alternatively, per-channel lead transfers using multiple overlay cables to the 64-channel chip are possible, although not preferable. This integration approach, along with the components involved, is shown in FIG. 29. The package is made compact by placing the components as close to each other as possible, as shown in FIG. 29, eliminating the routing lines from the platform. An etched cavity holds the chip such that no components protrude vertically. The cable is also kept compact by making use of the area on top of the chip to route all the leads. The other end of the cable would go to the rest of the microsystem circuitry, but in this case it is designed to be bonded to a PCB connector to transfer power to the chip and outputs from the chip.

The fabrication of the package starts with a standard silicon wafer approximately 500 µm thick. The first step is to lithographically pattern the front side of the wafer and deposit and liftoff chromium (300 Å) and gold (5000 Å) for the bonding pads between the slots of the 3-D array. Then, the chip cavity is patterned and DRIE etched from the front side to a depth of about 300 µm, which is the thickness of the chip coming from the MOSIS foundry. This cavity opening, measuring 2.2 mm×1.5 mm, includes a 150 µm tolerance all around to account for size differences from chip to chip and for positioning during assembly. Next, the wafer is patterned to define the front-side slot regions and perimeter openings. The challenge here is to conformally coat the photoresist around a 300 µm deep cavity. Since the cavity opening is relatively large, conformal coating was achieved using a non-standard resist spread/spinning technique. This technique involves using a very viscous photoresist (AZ 9260) with a slow and long spread time (500 rpm for 1 min), followed by a spin/dry step (500 rpm for 1 min). This technique was characterized to allow the edges of the cavity to remain protected with resist. The slots and perimeter of the package are then DRIE etched to a depth of 300 µm, which is the height of the probe back end. Since the front-side slot/perimeter depth and the chip cavity depth are the same in this design, a single-step lithography for the front-side etch (cavity and slots) was explored. However, due to the significant differences in the mask opening and aspect ratio, an optimal DRIE etch recipe was not achieved. The difficulty is that the chip cavity was found to etch at nearly twice the rate as the narrow slots, requiring a two step front-side etch. The simplest method for a two step front-side etch is to use the spin technique just described, but a more complicated method involving a shadow mask could also be explored for patterning a deep etched wafer. The final step is to pattern the back side of the wafer and DRIE etch the slots and perimeter (~200 µm) until the platform is released from the wafer. The platforms are soaked in acetone to remove the photoresist and cleaned with IPA. The top and cross-sectional views of the chip cavity region of the platform are shown in FIGS. 30(a)-(b), respectively, along with a top view of the populated cavity in FIG. 30(c).

In the assembly of this front-end, the 16-channel passive silicon probes with gold plated tabs on the back end are used. First, the probes (4 in parallel) are assembled in the platform using a brass jig and ultrasonically bonded to the pads. These tabs are designed to cover only half of the bonding pad as shown in FIG. 31(a); the other half is used to bond the tab from the overlay cable. Next, the chip is separately secured on a glass slide using a temporary adhesive and the overlay cable is aligned and tab bonded on one end to the bonding pads on the chip.

At this point, the chip/cable connections are tested for electrical continuity on a probe station. The measured interconnect resistance for this 1.5 cm cable with 10 µm wide lines is approximately 300 Ω. Following successful testing, the chip is removed from its temporary fixture and moved, along with the bonded cable, into its cavity on the silicon platform. The bottom of the cavity should have a very small amount of silastic that cures over a period of several hours to allow for adjustment during bonding but to eventually secure the chip in place. With the platform fully populated, the chip/cable assembly is adjusted in the cavity so that the front part of the cable is aligned to the probe tab array and ultrasonically tab bonded. The tabs from the cable are designed to fold down towards the probe tabs onto the other half of the platform bonding pad as shown in FIG. 31(b). Vertically stacked tabs from the probe/cable could also be designed in future versions but would require the chromium (from the seed layer) to be etched from the backside of the tabs. Notice that the interconnect lines are routed to make maximum use of the spacing between probe slots as they run directly on top of slots and other bonding pads. Finally, the back end of the cable is mounted to an acute PCB and wire bonded for power and output leads. The completed platform is removed from the brass assembly jig, ready for testing. Details of the tab bonding of probes/cable onto the platform are shown in the pictures of FIG. 32. The final integrated device is shown in its most compact form in the photograph of FIG. 33.

In summary, the present disclosure presents a new integration method for fully-implantable Microsystems. This method eliminates the interconnect routing conventionally fabricated on the supporting platform allowing components to be arranged in the most compact configurations. The surface area (size) of the microsystem can be significantly reduced and is only limited by the number/size of the components themselves. The electrical lines are carried by a flexible polymer cable (Parylene-C in this work) that is placed directly on top of the components. The interconnect lines on the cable terminate in beam leads that are ultrasonically bonded to the component bondpads. This integration method was applied to the front-end of a neural recording microsystem. The ultrasonically bonded overlay cable approach was validated in-vivo by recording neural signals using passive probes connected the chip while the power and data transfer to and from the chip were carried by the parylene cable. This integrated front-end achieves the most compact low-profile fully-implantable microsystem with zero-rise above the surface of the platform.

It is anticipated that in other versions of the full microsystem, the remaining components can be integrated on a separate (satellite) platform using a similar approach. The overlay cable can be extended to accommodate the integration of the satellite platform and connected to the front-end platform. Multiple overlay cables can be stacked to aid in simplifying the design and bonding of high-channel count Microsystems with single/multiple components with a negligible cost in vertical rise. This allows not only compact lateral integration but also a physical separation, reducing the electromagnetic interference generated by the wireless components in the microsystem from the sensitive analog front-end. The entire package, except the electrodes, should finally be encapsulated with a biocompatible material such as parylene.

What is claimed is:

1. A microsystem comprising:
   a substrate having an aperture formed therethrough, said aperture having a first cross-section and a second cross-section, said first cross-section being smaller than said second cross-section to define a ledge therebetween, said ledge being disposed within said aperture;
   a probe member disposed within said aperture of said substrate, said probe member having a back end, said back end defining a cross-section that is greater than said first cross-section of said aperture and smaller than said second cross-section such that said probe member engages said ledge; and
   a plurality of probe shanks extending from said probe member, each of said probe shanks having a plurality of independent electrode leads disposed therealong, each of said leads extending from said probe shanks to said back end of said probe member.

2. The microsystem according to claim 1, further comprising:
   a cable overlay electrically coupled to said leads on said back end of said probe member.

3. The microsystem according to claim 2 wherein said cable overlay comprises:
   a first polymer layer;
   a second polymer layer coupled to said first polymer layer; and
   metallic lines disposed between said first polymer layer and said second polymer layer.

4. The microsystem according to claim 3 wherein said metallic lines comprise tab portions extending within cutout regions formed in said first polymer layer and said second polymer layer, said tab portions being electrically coupled to said leads on said back end of said probe member.

5. The microsystem according to claim 2, further comprising:
   onboard circuitry disposed on said cable overlay, said onboard circuitry being electrically coupled with at least one of said plurality of probe shanks.

6. The microsystem according to claim 2 wherein said cable overlay is disposed upon said substrate and is substantially parallel thereto.

7. A 3-D neurostructure microsystem comprising:
   a substrate having an aperture formed therethrough, said aperture having a ledge portion formed internally in said aperture;
   a neuro-probe member disposed within said aperture of said substrate, said probe member having a back end, said back end being substantially received within said aperture, said probe member engaging said ledge portion and being supported thereby; and
   a plurality of probe shanks extending from said probe member, each of said probe shanks having a plurality of independent electrode leads disposed therealong, each of said leads extending from said probe shanks to said back end of said probe member.

8. The 3-D neurostructure microsystem according to claim 7, further comprising:
   a cable overlay electrically coupled to said leads on said back end of said probe member.

9. The 3-D neurostructure microsystem according to claim 8 wherein said cable overlay comprises:
   a first polymer layer;
   a second polymer layer coupled to said first polymer layer; and
   metallic lines disposed between said first polymer layer and said second polymer layer.

10. The 3-D neurostructure microsystem according to claim 9 wherein said metallic lines comprise tab portions extending within cutout regions formed in said first polymer layer and said second polymer layer, said tab portions being electrically coupled to said leads on said back end of said probe member.

11. The 3-D neurostructure microsystem according to claim 8, further comprising:
   onboard circuitry disposed on said cable overlay, said onboard circuitry being electrically coupled with at least one of said plurality of probe shanks.

12. The 3-D neurostructure microsystem according to claim 8 wherein said cable overlay is disposed upon said substrate and is substantially parallel thereto.

13. The 3-D neurostructure microsystem according to claim 8 wherein said onboard circuitry comprises signal processing capability.

14. The 3-D neurostructure microsystem according to claim 8 wherein said onboard circuitry comprises telemetry capability.

15. The 3-D neurostructure microsystem according to claim 7 wherein said substrate defines a footprint of 1 mm by 1 mm or smaller.

* * * * *